US007105095B2

(12) United States Patent
Yano et al.

(10) Patent No.: US 7,105,095 B2
(45) Date of Patent: Sep. 12, 2006

(54) METHOD AND APPARATUS FOR CONTROLLING CONCENTRATION OF WATER TREATMENT CHEMICALS

(75) Inventors: Daisaku Yano, Tokyo (JP); Toshiharu Wake, Tokyo (JP); Kiyotaka Yamamura, Tokyo (JP); Hiro Yoshikawa, Tokyo (JP)

(73) Assignee: Organo Corporation, Tokyo (JP)

( * ) Notice: Subject to any disclaimer, the term of this patent is extended or adjusted under 35 U.S.C. 154(b) by 130 days.

(21) Appl. No.: 10/826,675

(22) Filed: Apr. 16, 2004

(65) Prior Publication Data

US 2004/0262233 A1 Dec. 30, 2004

Related U.S. Application Data

(60) Provisional application No. 60/556,410, filed on Mar. 25, 2004.

(30) Foreign Application Priority Data

Apr. 17, 2003 (JP) ............................. 2003-113283

(51) Int. Cl.
*C02F 1/00* (2006.01)

(52) U.S. Cl. ................... 210/739; 210/745; 210/746; 210/749; 210/143; 210/198.1

(58) Field of Classification Search ............... 210/745, 210/746, 739, 749, 143, 198.1; 436/55; 204/418
See application file for complete search history.

(56) References Cited

U.S. PATENT DOCUMENTS

| 4,992,380 A | * | 2/1991 | Moriarty et al. ............... 436/55 |
| 6,508,921 B1 | * | 1/2003 | Mu et al. ..................... 204/418 |

FOREIGN PATENT DOCUMENTS

| JP | 51-111388 | 10/1976 | |
| JP | 60202875 A | * 10/1985 | ................. 549/353 |
| JP | 2-115697 | 4/1990 | |
| JP | 4-296651 | 10/1992 | |
| JP | 4-296652 | 10/1992 | |
| JP | 6-73045 | 3/1994 | |
| JP | 2001-4585 | 1/2001 | |
| JP | 2001-334255 | 12/2001 | |

OTHER PUBLICATIONS

Kazahiko Watanabe et al. "Lithium Ion Selective Optical Sensor Based on a Novel Neutral Ionophore and a Lipophilic Anionic Dye" Anal Chem. 1993, 65, 2704-2710.

Koji Suzuki et al, "Design and Synthesis of Highly Selective Ionophores for Lithium on Based on 14-Crown-4 Derivatives for an Ion-Selective Electrode" Anal Chem. 1993, 65, 3404-3410.

(Continued)

*Primary Examiner*—Robert A. Hopkins
(74) *Attorney, Agent, or Firm*—Osha Liang LLP

(57) ABSTRACT

A water-soluble lithium salt is added as a tracer substance along with a water treatment chemical to water to be treated. The concentration of lithium ions is electrochemically or optically measured using a lithium ion sensitive substance, so as to perform concentration control of the water treatment chemical added to water to be treated. An ion selective electrode, ion selective field effect transistor, or ion optode may be employed to perform the electrochemical or optical measurement using a lithium ion sensitive substance.

15 Claims, 14 Drawing Sheets

OTHER PUBLICATIONS

English Abstract of Publication No. 2-115697 (1 page).
English Abstract of Publication No. 2001-334255 (1 page).
English Abstract of Publication No. 4-296651 (1 page).
English Abstract of Publication No. 4-296652 (1 page).
English Abstract of Publication No. 51-111388 (1 page).
English Abstract of Publication No. 6-73045 (1 page).
English Abstract of Publication No. 2001-4585 (1 page).

* cited by examiner

METHOD AND APPARATUS FOR CONTROLLING CONCENTRATION OF WATER TREATMENT CHEMICALS

CROSS-REFERENCE TO RELATED APPLICATIONS

This application claims priority, pursuant to 35 U.S.C. § 119 to U.S. Provisional Application No. 60/556,410, entitled "Method and Apparatus for Controlling Concentration of Water Treatment Chemical," filed Mar. 25, 2004.

BACKGROUND OF THE INVENTION

1. Field of the Invention

The present invention relates to a method and apparatus for controlling concentration of a water treatment chemical (a water treating chemical agent or a chemical additive to a water system) within water of a recirculating water system such as a cooling water system.

2. Description of the Related Art

Process water such as industrial water serves a significant role in many industries. Process water is often used in a recirculating water system, which may typically be a boiler water system or an open or closed recirculating cooling water system. For treating water used in such a recirculating water system, various water treatment chemicals (chemical agents) are employed to prevent problems such as corrosion, scale, and slime attributable to by water. In general, water treating chemical agents may include a corrosion inhibitor, dispersant, scale inhibitor, antimicrobial, and slime control agent (biofouling inhibitor).

In order to perform appropriate water treatment by making use of the effectiveness of these various chemical agents and to allow the effectiveness to sustain, it is necessary to precisely determine the concentration of the chemical agents at given positions and times, so as to execute appropriate control of the concentration.

However, measurement of concentration within water to be treated is impossible for some chemicals, depending on the type of the chemical. Further, although the measurement may be possible by colorimetry, turbidimetry, or other quantitative analysis methods, procedures for these methods may be complicated or require a long time such that the methods are impractical for plant operation control. Accordingly, when using a water treatment chemical for which concentration measurement is impossible or difficult, concentration control may be performed using, as a tracer, a substance that allows easy concentration measurement. By using a tracer substance, concentration of a chemical agent within water to be treated can be indirectly but quickly measured even when concentration measurement of the chemical agent itself is impossible or difficult. Conventional methods for measuring the concentration of a water treatment chemical using a tracer substance may be categorized by the type of tracer substance. Major examples of the tracer methods are fluorescent tracer method, pigment tracer method, bromine tracer method, iodine tracer method, potassium tracer method, and lithium tracer method.

It is generally desired that a substance used as a tracer fulfill many conditions as listed below. (1) The substance does not exist in process service water such as industrial water, or the amount of its presence in water is a negligibly trace amount. (2) The substance is chemically stable. (3) The substance is not easily decomposed by microorganisms. (4) The substance is substantially harmless from a pollution prevention perspective. (5) The substance does not generate insoluble matters or scale by reacting with salts dissolved in process water such as industrial water. (6) The substance does not corrode the metal materials of the piping and other components of the water system. (7) The quantitative analysis of the substance is possible without being interfered by dissolved salts. (8) The quantitative analysis can be performed precisely and quickly.

Among the conventional methods for measuring concentration of a water treatment chemical, a fluorescent tracer method is disclosed in Japanese Patent Laid-Open Publication No. Hei 2-115697, while a pigment tracer method is disclosed in Japanese Patent Laid-Open Publication No. 2001-334255. According to these methods, many of the organic substances employed as the tracer tend to degenerate by the influence of light, heat, oxidants, pH, and the like within the recirculated water such as boiler water or cooling water (especially cooling water in an open recirculating system). Consequently, measurements as a function of time of the tracer concentration tends to a decrease irrespective of the water treatment chemical concentration, resulting in the problem that the tracer concentration cannot be correctly converted into the water treatment chemical concentration. Further, the recirculated water including water treatment chemicals in addition to the tracer may contain, at varying degrees, a light-absorbing substance or a fluorescent substance generated due to fouling such as sludge. As a result, measurements must be made taking into account the interferences from those matters.

As another conventional method for measuring concentration of a water treatment chemical, a method using bromide ion or iodide ion as the tracer is disclosed in Japanese Patent Laid-Open Publication No. Hei 4-296651. This publication describes using titration and ion electrode method for quick and simple measurement of bromine or iodine, and using ion chromatography when requiring high sensitivity or simultaneous measurement of other anions. However, procedures for titration are complicated, and it would be very difficult to automate titration analysis. Real-time concentration control by titration is therefore impossible at the present. Further, bromide ion electrode method and iodide ion electrode method are disadvantageous in their poor selectivity with respect to other anions and the susceptibility to interferences from impurities contained in the cooling water. Ion chromatography requires a large-scale instrument, as well as a long time from the point when sample water is collected to the point when a measurement result can be obtained, so that real-time concentration control is impossible.

A potassium tracer method is disclosed in Japanese Patent Laid-Open Publication No. Hei 4-296652. This publication suggests use of an ion electrode method as the quick and simple measurement method. However, a certain amount of potassium ion is originally included in the raw water of the cooling water. The potassium tracer method is therefore susceptible to influences from fluctuations in the concentration of potassium included in the raw water supplied as the make-up water for the cooling water.

A lithium tracer method is disclosed in Japanese Patent Laid-Open Publication No. Sho 51-111388. This method requires performing atomic absorption spectrometry, which involves using a large-scale instrument. Further, because a long time is required from the point when sample water is collected to the point when a measurement result can be obtained, real-time concentration control is impossible.

SUMMARY OF THE INVENTION

According to the present invention, a water-soluble lithium salt is added as a tracer substance along with a water treatment chemical to water to be treated. The concentration of the lithium ions is electrochemically or optically measured using a lithium ion sensitive substance. The measured lithium ion concentration is used to control the concentration of the water treatment chemical added to the water to be treated.

The lithium ion concentration may be measured by detecting a membrane potential indicated by a lithium ion electrode incorporating a sensitive membrane including the lithium ion sensitive substance, by detecting a change in a value of current flowing in a field effect transistor incorporating the lithium ion sensitive substance, or by detecting an optical characteristic indicated by a membrane incorporating the lithium ion sensitive substance and a fluorescent or light-absorbing substance. Preferably, the water-soluble lithium salt is added so that the lithium ion concentration in the water to be treated is within the range of 0.01–20 mg/liter.

By performing lithium ion detection using a lithium ion selective substance in this manner, the lithium ion concentration can be easily measured, and the measurement result can be employed to perform an appropriate control of the water treatment chemical concentration.

DESCRIPTION OF THE PREFERRED EMBODIMENTS

Figure 1:
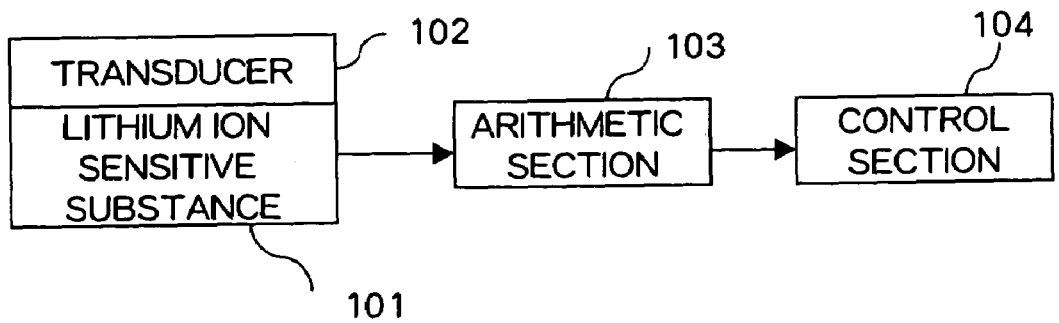
FIG. 1 is a schematic diagram showing a configuration of an apparatus for controlling concentration of a water treatment chemical according to an embodiment of the present invention.

A preferred embodiment of the present invention will next be described. According to the present embodiment, a known amount of water-soluble lithium salt is added along with a known amount of water treatment chemical to water in a recirculating water system such as a cooling water system. A lithium ion sensitive substance is used to detect the concentration of lithium ions within the recirculating water system. Based on the detected lithium ion concentration proportional to the known amount of water treatment chemical, the concentration of the water treatment chemical present within the water is determined. Using the information obtained in this manner, concentration of the water treatment chemical present within the water of the recirculating water system can be detected, allowing control of the water treatment chemical concentration.

Lithium ions do not normally exist in process water such as industrial water, chemically stable, unsusceptible to influences from microorganisms, substantially harmless in the concentration used, and do not cause scale problems due to their chemical property. By using a lithium ion sensitive substance according to the present invention, lithium ion concentration can be determined much more easily in a shorter time compared to a conventional method such as atomic absorption spectrometry. Further, according to the present invention, a measurement can be made on-site using a simple measurement device.

Examples of a water-soluble lithium salt used may include, without limitation, lithium carbonate, lithium hydroxide, lithium sulfate, and lithium chloride.

According to the present embodiment, a lithium ion is added as a tracer substance by an amount proportional to the added amount of a water treatment chemical. The lithium ion and the water treatment chemical may be added separately to water to be treated at a predetermined ratio with respect to one another, or alternatively, the lithium ion tracer and the water treatment chemical may be mixed in advance at a predetermined ratio and simultaneously added to water to be treated.

In one method for calculating concentration of the water treatment chemical, the ratio between the amount of water treatment chemical and the amount of lithium ion tracer added to the water system is determined in advance as the known coefficient (chemical concentration conversion coefficient for lithium ion tracer). Subsequently, the concentration of the lithium ion tracer within water to be treated is detected at an appropriate sampling position and time. The detected lithium ion concentration value and the coefficient may be multiplied to calculate the water treatment chemical concentration. Based on the calculated value, the necessary amount of water treatment chemical and lithium ion tracer to be added to water to be treated can be determined.

A typical example of a lithium ion sensitive substance is an ion selective coordination molecule (also referred to as an ionophore or neutral carrier) which selectively forms a coordinate bond with a lithium ion. An ion selective coordination molecule selectively forming a coordinate bond with a lithium ion according to the present invention may include, for example, 6,6-dibenzyl-1,4,8,11-tetraoxacyclotetradecane (CAS No. 106868-21-7), 6-[2-(diethoxyphosphoryloxy)ethyl]-6-dodecyl-1,4,8,11-tetraoxacyclotetradecane, and compounds denoted by chemical formula (1) or (2) below:

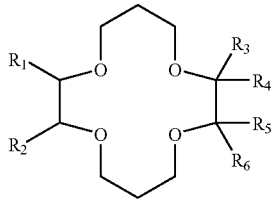

(1)

(wherein $R_1$ and $R_2$ are independent from one another, each consisting of a hydrogen atom, alkyl group, benzyl group, benzyloxymethyl group, phenyl group, or cyclohexyl group, and each of $R_3$–$R_6$ is an independent hydrocarbon group), or

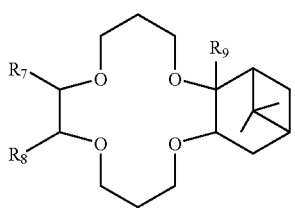

(2)

(wherein each of $R_7$–$R_9$ is an independent hydrogen atom or hydrocarbon group, while at least one of $R_7R_9$ is a hydrocarbon group).

The number of carbon within each alkyl group at $R_1$ and $R_2$ and each hydrocarbon group at $R_3$–$R_6$ and $R_7$–$R_9$ is preferably within the range from 1 to 28. Further, each of the above-defined compounds preferably includes at least one alkyl or hydrocarbon group having a long carbon chain composed of four or more carbons. Specific examples of the compound of chemical formula (1) include trans-2,3-dibenzyloxamethyl-9,9,10,10-tetramethyl-1,4,8,11-tetraoxacylotetradecane (disclosed in Japanese Patent Laid-Open Publication No. Hei 6-73045), and 2,2,3,3-tetramethyl-9-tetradecyl-1,4,8,11-tetraoxacylotetradecane (CAS No. 151460-00-3). One specific example of the compound of chemical formula (2) is (1R,14S,16R,18R)-1,17,17-trimethyl-7-tetradecyl-2,6,9,13-tetraoxatricylo-[12.4.0.1$^{16.18}$]octadecane.

6,6-dibenzyl-1,4,8,11-tetraoxacyclotetradecane is denoted by chemical formula (3) below.

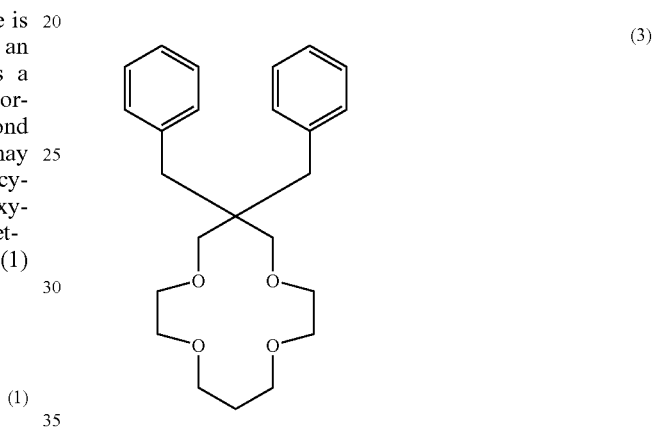

(3)

2,2,3,3-tetramethyl-9-tetradecyl-1,4,8,11-tetraoxacylotetradecane is denoted by chemical formula (4).

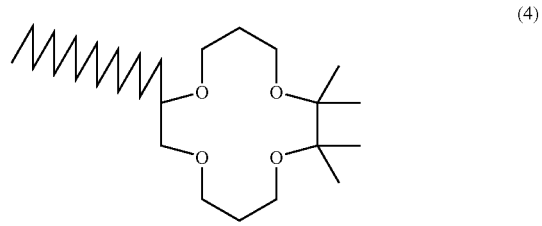

(4)

(1R,14S,16R,18R)-1,17,17-trimethyl-7-tetradecyl-2,6,9,13-tetraoxatricylo-[12.4.0.1$^{16.18}$]octadecane is denoted by chemical formula (5).

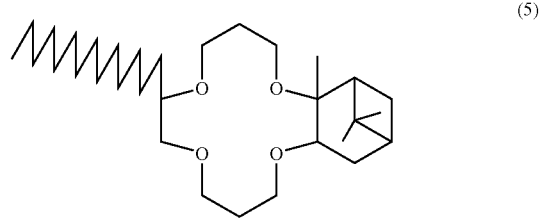

(5)

6-[2-(diethoxyphosphoryloxy)ethyl]-6-dodecyl-1,4,8,11-tetraoxacyclotetradecane is denoted by chemical formula (6).

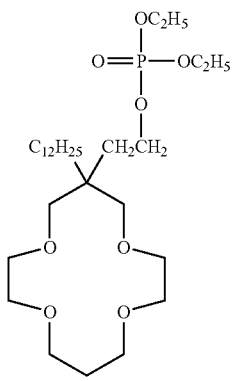

(6)

The lithium ion concentration may be measured by detecting a membrane potential indicated by a membrane electrode having a sensitive membrane including a lithium ion sensitive substance. A lithium ion electrode incorporating the sensitive membrane is one type of lithium ion sensor which functions as an ion selective electrode that is selective to lithium ions. In general, an ion selective electrode is a membrane electrode which can measure target ions dissolved in a solution according to an indicated membrane potential, allowing easy, quick, and selective ion measurement. As described below in detail, particularly excellent results with respect to water to be treated in a recirculated water system such as a cooling water system can be obtained when a compound of chemical formula (1) or (2) is used as the lithium ion sensitive substance in the lithium ion electrode.

Figure 15:
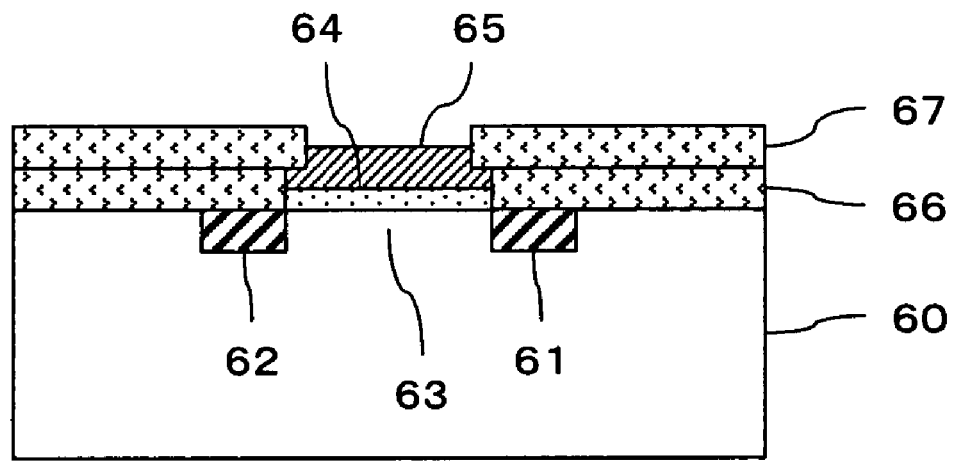
FIG. 15 is a diagram showing a structure of an ion selective field effect transistor incorporating a lithium ion selective membrane.

According to an alternative method, the lithium ion concentration may be measured using a field effect transistor incorporating a lithium ion sensitive substance. This field effect transistor is described referring to FIG. 15. In a surface of a silicon substrate 60, a drain region 61 and a source region 62 are formed by impurity injection. The region between the drain and source regions serves as the channel region 63. A lithium ion sensitive membrane 65 incorporating a lithium ion sensitive substance is provided, as agate electrode, over the channel region 63 via a gate insulation film 64. An insulation film 66 is formed on the sides of the gate insulation film 64 and the lithium ion sensitive membrane 65. A protection film 67 is further provided covering the insulation film 66 and peripheral portions of the lithium ion sensitive membrane 65.

The field effect transistor as described above is immersed in water to be measured, and a voltage is applied between the source 61 and drain 62 regions. The potential of the lithium ion sensitive membrane 65 changes in accordance with the lithium ion concentration in the water. Accordingly, the potential of the gate electrode changes in accordance with the lithium ion concentration in the water, resulting in a change in the current flowing between the source 61 and drain 62 regions. By detecting this current, the lithium ion concentration can be determined.

As such, the field effect transistor functions as an ion selective field effect transistor which selects, in this case, lithium ions. A field effect transistor as described above is described in documents such as Japanese Patent Laid-Open Publication No. 2001-4585.

According to another method as disclosed in Anal. Chem., 65, 2704–2710 (1993), the lithium ion concentration may be measured by detecting an optical characteristic indicated by a membrane composed of a lithium ion sensitive substance and a fluorescent or light-absorbing substance. This membrane functions as a lithium ion sensitive membrane. A light-detecting chemical sensor employing this membrane is referred to as an ion optode (disclosed in Japanese Patent Laid-Open Publication No. 2001-108621). For example, an electrically neutral ionophore and a color-changing pigment may be employed to form the sensitive membrane. When a lithium ion bonds to the ionophore, the ionophore discharges a proton, for example, and this proton may attach to the color-changing pigment, causing a color change. By irradiating a visible light or the like on the sensitive membrane to measure absorbance of a predetermined wavelength of the changed color pigment, the lithium ion concentration can be determined.

Figure 16:
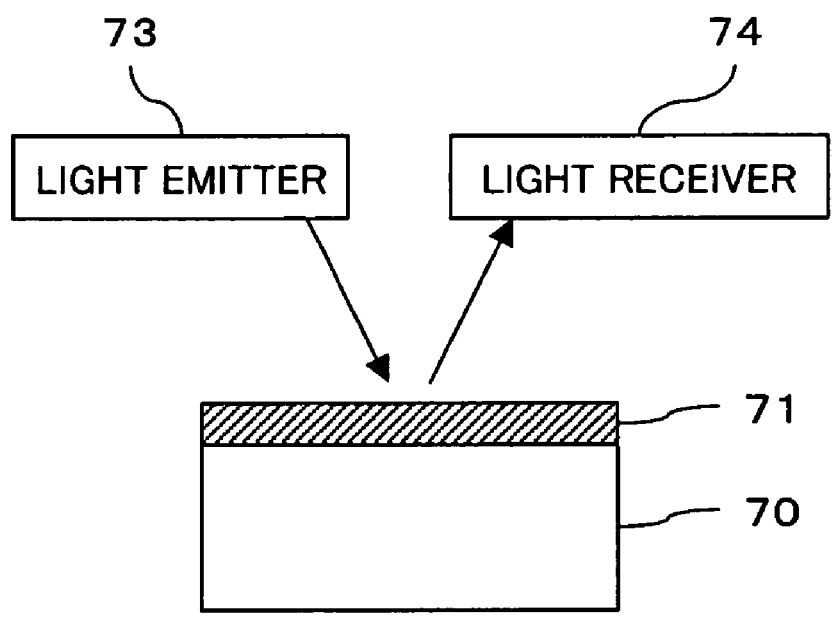
FIG. 16 is a diagram showing a configuration for measuring lithium ion concentration using changes in an optical characteristic of a lithium ion selective membrane.

More specifically, as shown in FIG. 16, a lithium ion sensitive membrane 71 incorporating a lithium ion sensitive substance is formed on a mirror 70. This mirror structure is immersed in water to be measured, and a light having a predetermined wavelength is irradiated by a light emitter 73 onto the lithium ion sensitive membrane 71. The irradiated light is transmitted through the lithium ion sensitive membrane 71, reflected by the mirror 70, retransmitted through the lithium ion sensitive membrane 71, and received by a light receiver 74. Because an optical characteristic of the lithium ion sensitive membrane 71 changes in accordance with the lithium ion concentration in the water, the lithium ion concentration in the water can be detected based on the intensity of light received by the light receiver 74.

A major example of the fluorescent substance is a fluorescein derivative such as 4',5'-dibromofluorescein octadecylester. As the light-absorbing substance, an oleophilic anion pigment such as N-2,4-dinitro-6-(octadecyloxy)phenyl-2',4'-dinitro-6'-(trifluoromethyl)phenylamine, disclosed in Anal. Chem., 65, 2704–2710 (1993), may be employed.

The lithium ion concentration within water to be treated such as cooling water is preferably within the range of approximately 0.01–20 mg/L because, even in such a low concentration range, the lithium ions sufficiently function as a tracer. Further, the calibration curve with respect to the lithium ion concentration normally exhibits sufficient repeatability in this low concentration range. At a concentration below 0.01 mg/L, the lithium ion sensitive membrane may not be able to function as desired. A concentration exceeding 20 mg/L would result in an increased amount of added water-soluble lithium salt, which is generally uneconomical. When employing a lithium ion electrode incorporating a sensitive membrane including a compound of chemical formula (1) or (2), the lithium ion concentration within water to be treated such as cooling water is more preferably within the range of 0.01–2 mg/L for further cost reduction. This lower concentration range is possible because such an electrode has particularly high sensitivity.

The amount of water treatment chemical added to water to be treated can be controlled using an apparatus for controlling water treatment chemical concentration according to the present invention. The apparatus comprises a lithium ion sensitive substance placed in contact with water to be treated, a transducer for converting a state of the sensitive substance into an electric or optical signal, an arithmetic section for receiving the signal and calculating a concentration of the water treatment chemical, and a control section for determining, based on the calculated water treatment chemical concentration, an amount of the water treatment chemical to be added to water to be treated. The arithmetic section may be configured such that a receiver portion can be regarded as a separate portion, or alternatively, the receiver portion may be an integral and inseparable portion of the arithmetic section.

FIG. 1 is a schematic diagram for explaining the configuration of the apparatus for controlling concentration of a water treatment chemical. The lithium ion sensitive substance 101 as described above is arranged in contact with water to be treated. The transducer 102 converts a state of the lithium ion sensitive substance 101 into an electric or optical signal. When an ion selective electrode (lithium ion electrode) is used, a membrane potential obtained in comparison to a reference electrode is output as an analog or digital signal. When an ion selective field effect transistor is used, a current that flows in the transistor is output as an analog or digital signal. When an optical characteristic is detected using a membrane incorporating a lithium ion sensitive substance and a fluorescent or light-absorbing substance, a fluorescence intensity or absorbance is output as an analog or digital signal. The arithmetic section 103 converts the signal supplied from the transducer 102 into a lithium ion concentration within water to be treated, using a calibration curve stored in advance. The control section 104 calculates a dosage level of water treatment chemical using the lithium ion concentration obtained in the arithmetic section 103, and performs drive control, via a control line (not shown), of a component such as a pump (not shown) for adding the water treatment chemical. The arithmetic section 103 and the control section 104 may be configured as one unit, and preferably comprise a programmable controller, computer, or the like. From the sensitivity perspective, it is preferable to use a lithium ion electrode in the above arrangement.

Figure 2:
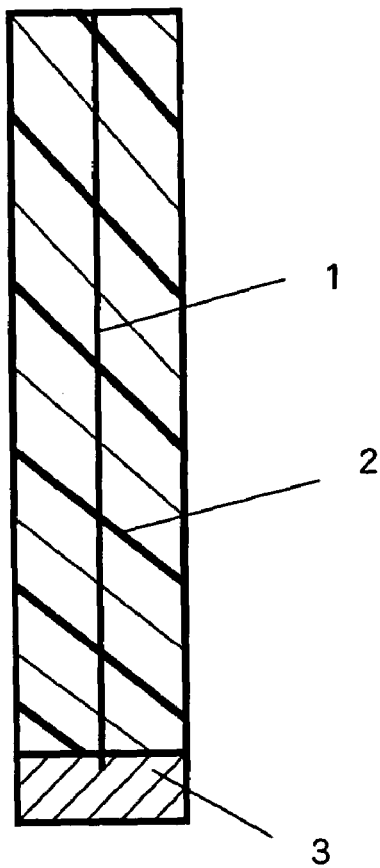
FIG. 2 is a schematic cross-sectional view showing an example structure of a lithium ion electrode.

FIG. 2 is a schematic view showing an example structure of the lithium ion electrode serving as a lithium ion sensor. The lithium ion electrode is formed by covering a plastic outer tube 2 over an electrode line 1. A lithium ion sensitive membrane 3 is formed at an end of the electrode line 1. The lithium ion sensitive membrane 3 is a liquid membrane containing lithium ion selective coordination molecules which selectively form coordinate bonds with lithium ions. The lithium ion sensitive membrane 3 is adhered to an end portion of the plastic outer tube 2. If necessary, an elastic plastic member or the like may be used to fix the lithium ion sensitive membrane 3 onto the end portion of the plastic outer tube 2. As long as an electrical connection can be formed between the electrode line 1 and the lithium ion sensitive membrane 3, the electrode line 1 may be simply placed in contact with the membrane 3. The above-described electrode structure is very similar to typical ion electrodes, but is unique in the use of the lithium ion sensitive membrane 3.

Figure 3:
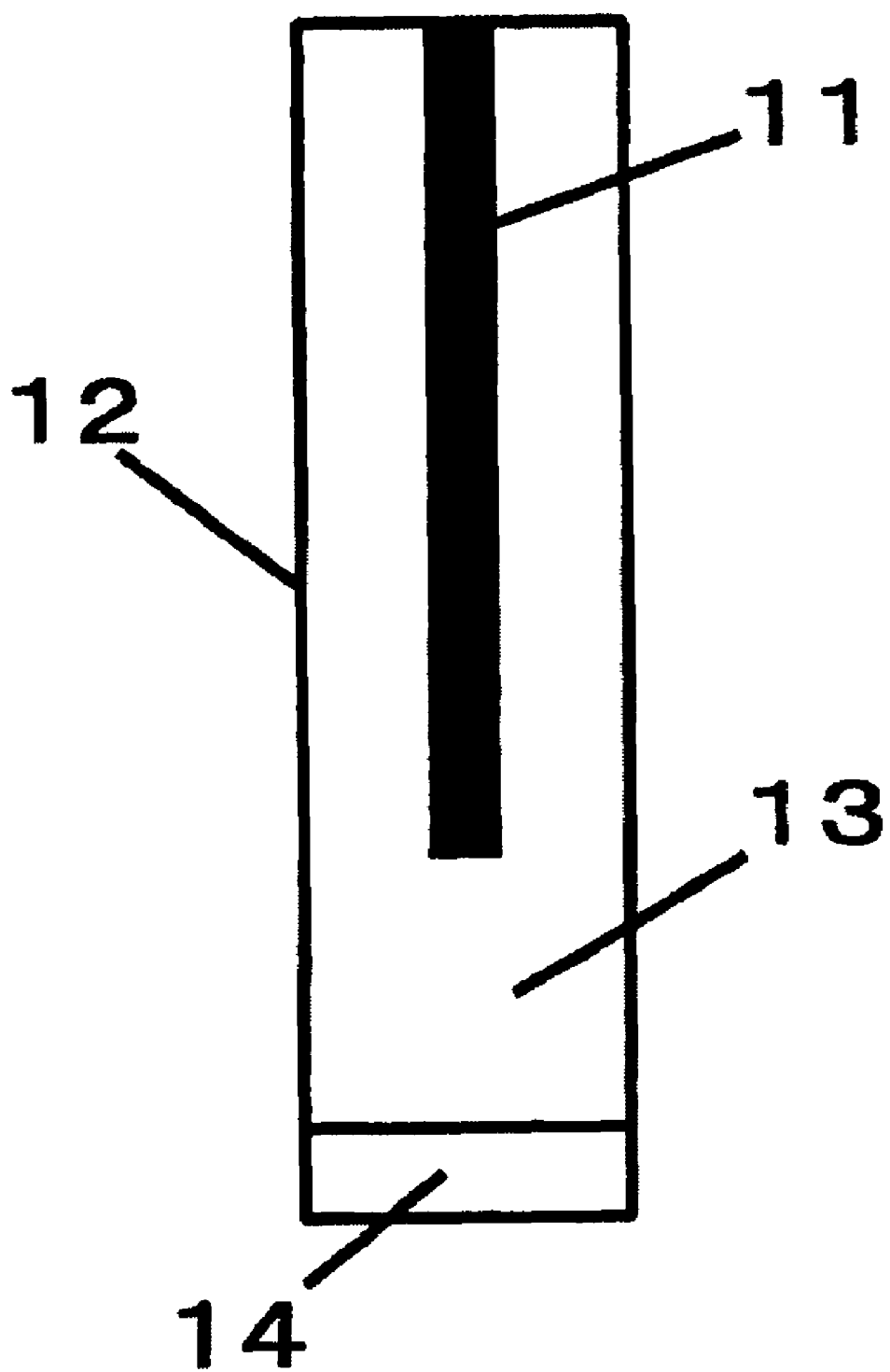
FIG. 3 is a schematic cross-sectional view showing another example structure of a lithium ion electrode.

FIG. 3 is schematic cross-sectional view showing another example structure of the lithium ion electrode. The lithium ion electrode includes, inside an outer tube 12, an internal solution 13, a lithium ion sensitive membrane 14 composed of a liquid membrane containing lithium ion selective coordination molecules which selectively form coordinate bonds with lithium ions, and an internal reference electrode 11. The internal solution 13 may be a solution containing lithium ions. For example, a lithium chloride solution of 0.001–1 mol/L may be favorably employed. The internal reference electrode 11 should stably operate within the internal solution 13, and may preferably comprise a silver-silver chloride electrode.

Figure 4:
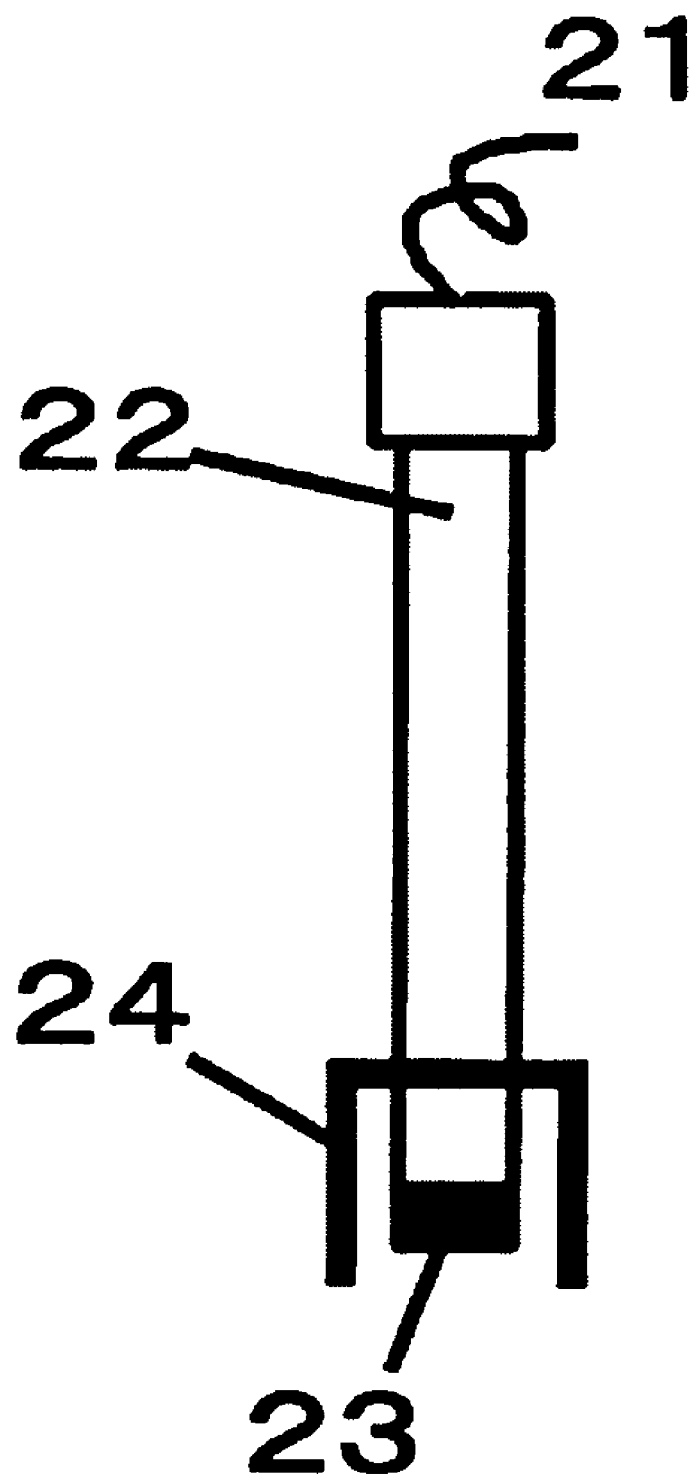
FIG. 4 is a schematic cross-sectional view showing a lithium ion electrode with its sensitive membrane portion covered with a box-shaped or tubular light-shielding cover.
Figure 5:
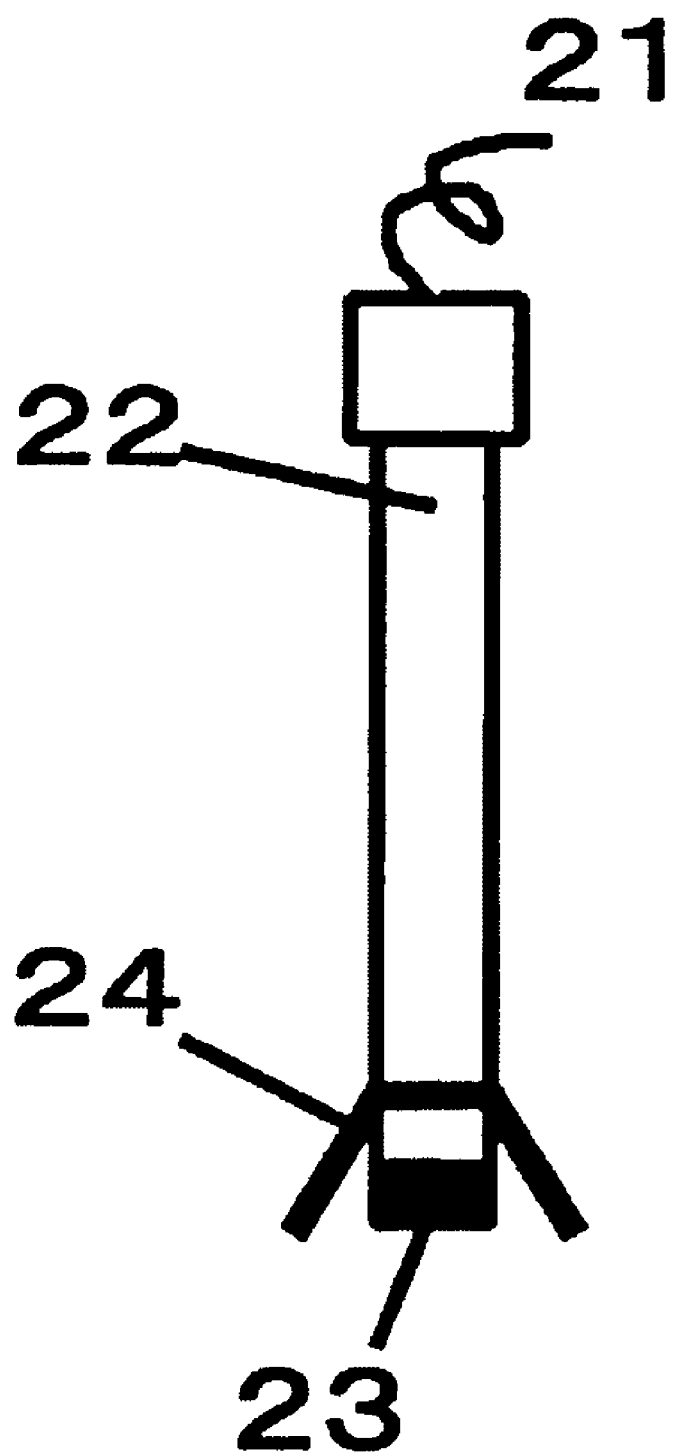
FIG. 5 is a schematic cross-sectional view showing a lithium ion electrode with its sensitive membrane portion covered with an umbrella-shaped light-shielding cover.
Figure 6:
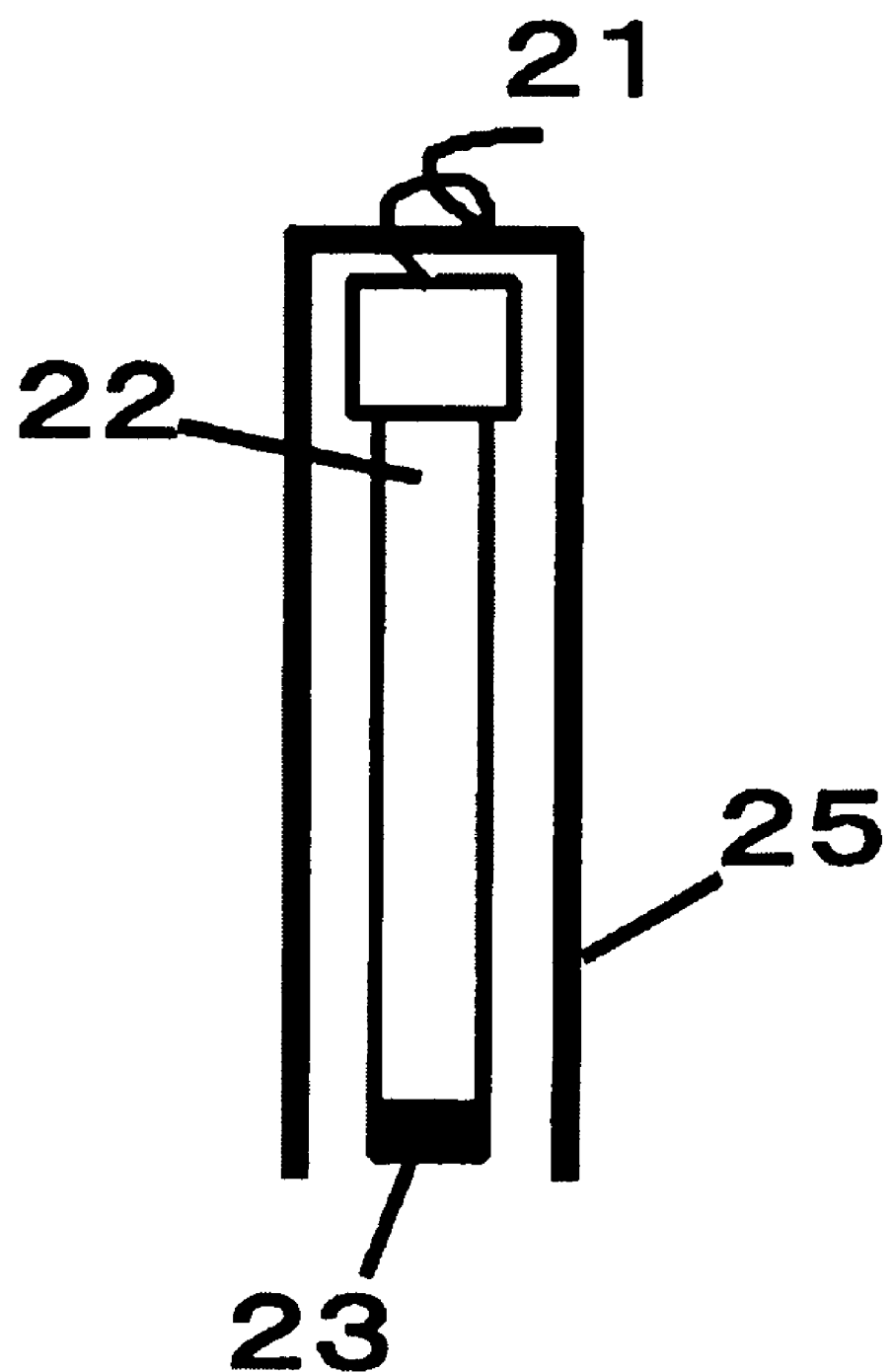
FIG. 6 is a schematic cross-sectional view showing a lithium ion electrode entirely covered with a box-shaped or tubular light-shielding cover.

It is observed that a lithium ion electrode tends to degrade within cooling water, causing a durability problem. As a result of a research concerning the factors influencing durability of a lithium ion electrode, the present inventors discovered that a biofilm which attaches to the surface of the sensitive membrane of a lithium ion electrode has a significant influence on the durability, and that the amount of attached biofilm can be greatly reduced by shielding light reaching the sensitive membrane surface. Based on this discovery, the present inventors found that the durability problem can be resolved by providing a light-shielding cover arranged so as to cover at least the sensitive membrane. The light-shielding cover may be configured to cover the sensitive membrane alone or the entire lithium ion electrode. The shape of the light-shielding cover is not limited, but may preferably be a box-shaped or tubular structure which covers the sensitive membrane alone as shown in FIG. 4, an umbrella-shaped structure which covers the sensitive membrane alone as shown in FIG. 5, or a box-shaped or tubular structure which covers the entire lithium ion electrode as shown in FIG. 6. The schematic cross-sectional views of FIGS. 4–6 show a signal line 21, lithium ion electrode 22, sensitive membrane 23, box-shaped or tubular or umbrella-shaped light-shielding cover 24 which covers the sensitive membrane alone, and box-shaped or tubular light-shielding cover 25 which covers the entire lithium ion electrode. The material constituting the light-shielding cover is not limited, as long as it has no negative influence on the lithium ion electrode and the cooling water system, and has durability within cooling water. A colored plastic, which may be black, or a metal may be favorably employed as the material for the light-shielding cover. It should be noted that, although an electrode line contacting the lithium ion sensitive membrane for extracting the membrane potential is not shown in FIGS. 4–6, the signal line 21 is actually connected to the lithium ion sensitive membrane 23 via an electrode line.

Next described in detail is a preferred embodiment according to the present invention using a lithium ion electrode incorporating a sensitive membrane including, as a lithium sensitive substance, a compound denoted by chemical formula (1) or (2). It should be noted that the present invention is not limited to this arrangement.

A boiler water system or an open or closed recirculating cooling water system generally employs water such as deionized water, tap water, and industrial water as the raw water, and operates at cycles of concentration ranging from 1 to 10. The cycles of concentration of the cooling water may constantly vary over time depending on the amount of evaporated water, blowdown, and make-up water. 6,6-dibenzyl-1,4,8,11-tetraoxacyclotetradecane is a readily available lithium ion sensitive substance. When there is little fluctuation in the quality of water to be treated, and especially when the cycles of concentration is not very high, a method using a lithium ion electrode incorporating a sensitive membrane including this substance as the lithium ion sensitive substance allows to detect a lithium ion tracer at a sufficiently high accuracy. However, it is observed that a response potential from a lithium ion electrode employing 6,6-dibenzyl-1,4,8,11-tetraoxacyclotetradecane as the lithium ion sensitive substance tends to be influenced by fluctuations in the characteristics of water to be treated, especially the cycles of concentration. Such an influence may possibly result in an unallowable error in a measured value of lithium ion concentration and inappropriate control of the water treatment chemical concentration. As a result of further research, the present inventors discovered that, using a lithium ion electrode incorporating a sensitive membrane employing a compound of chemical formula (1) or (2) as the lithium ion sensitive substance, the degree of influence on the response potential from fluctuations in the characteristics of water to be treated, especially the cycles of concentration, can be greatly reduced. The cycles of concentration may be calculated using the ratio of electric conductivity values of the raw water (make-up water) and the cooling water. Alternatively, the ratio of alkali metal ion concentration values or halogen ion concentration values of the raw water and the cooling water may be used to calculate the concentration ratio.

The measurement principle of the lithium ion electrode method is next described. A lithium ion electrode includes a sensitive membrane which selectively responds to lithium ions. When the sensitive membrane contacts lithium ions within a sample solution (sample water), a membrane potential corresponding to the lithium ion concentration is generated. In other words, the potential of the sensitive membrane changes in response to lithium ions in the sample water. A reference electrode immersed in the sample water is provided as a counter electrode of the lithium ion electrode. The reference electrode is connected to a direct current potentiometer having a high input impedance. Using this arrangement, a potential difference between the two electrodes can be measured so as to determine the membrane potential. The relative potential measured using the direct current potentiometer is referred to as the response potential. This arrangement is basically identical to various concentration meters. For example, a pH meter measures concentration of hydrogen ions by detecting, with respect to a reference electrode, a potential of an ion electrode which indicates a potential corresponding to a hydrogen ion concentration.

A relationship according to equation 1 exists between the response potential E and the lithium ion concentration [Li$^+$] within sample water. This equation is referred to as the Nernst equation.

$$E = E_0 + \frac{2.303RT}{F} \times \text{Log } [Li^+] \qquad \text{(Equation 1)}$$

Here, $E_0$ denotes the reference electrode potential at 25° C., R denotes the gas constant, T denotes absolute temperature, F the Faraday constant, and Log common logarithm. "2303RT/F" in equation 1 is called the Nernst constant. The value of this constant obtained when the lithium ion concentration is varied by a factor of 10 is referred to as the theoretical response gradient or Nernst gradient. For example, the Nernst gradient at 25° C. is approximately 59 mV.

When making a measurement using a lithium ion electrode, the relationship between the lithium ion concentration and the response potential is determined in advance by equation 2 below.

$$E = E_0 + S(T) \times \text{Log } [Li^+] \qquad \text{(Equation 2)}$$

The lithium ion concentration [Li+] within sample water can be determined based on the response potential E using equation 3 below.

$$[Li^+] = 10^{\frac{E-E_0}{S(T)}} \qquad \text{(Equation 3)}$$

Here, S(T) denotes the gradient of response potential E at water temperature T. Because lithium ion electrodes generally have individual differences, S(T) is not necessary identical to the theoretical value. Accordingly, it is preferable to determine S(T) for each lithium ion electrode using sample water having a known lithium ion concentration.

Figure 7:
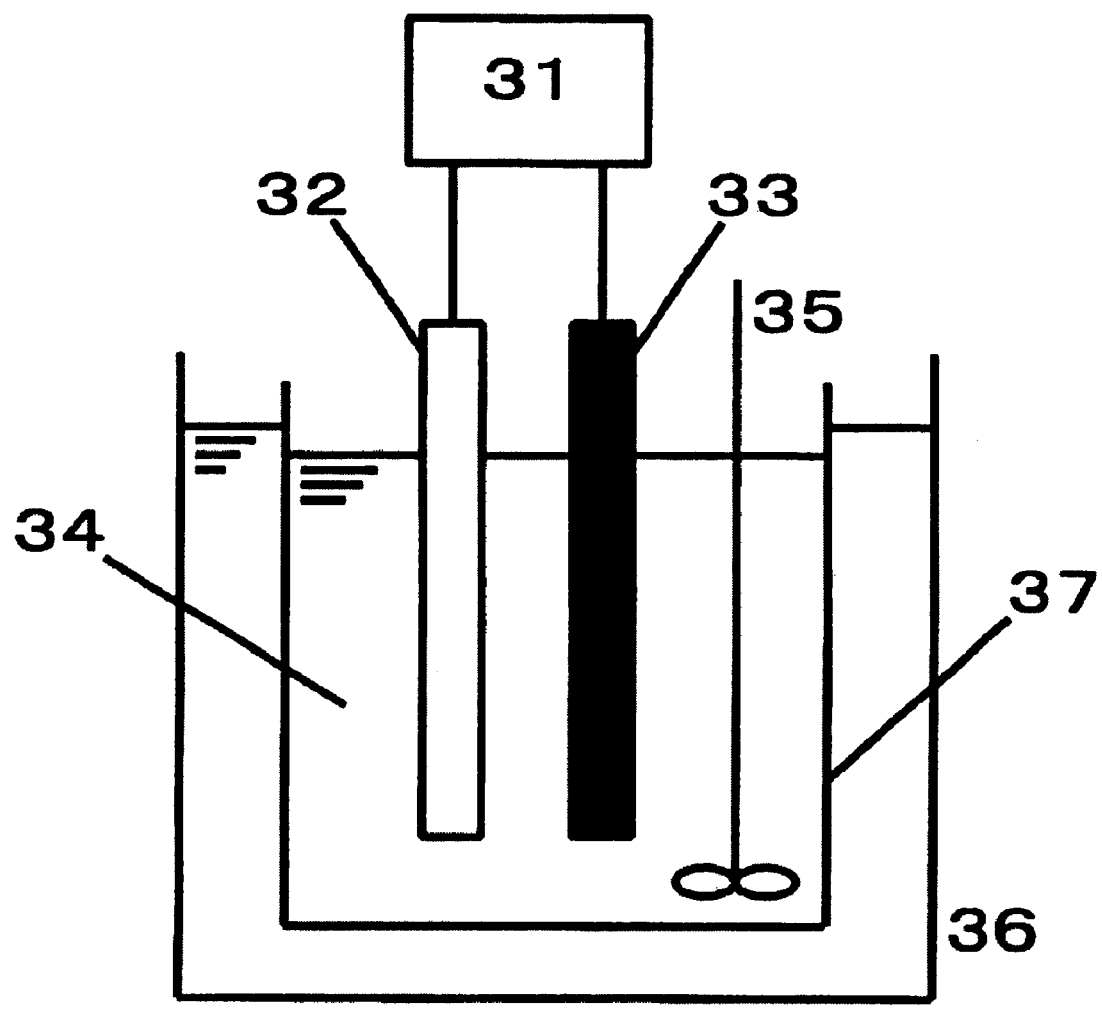
FIG. 7 is a schematic diagram showing an example configuration of a device for measuring a response potential using a lithium ion electrode.

FIG. 7 shows an example configuration of a device for measuring the response potential. A beaker 37 filled with sample water 34 is placed in a thermostatic bath 36. A lithium ion electrode 32 and its counter electrode, or reference electrode 33, is immersed in the sample water. Using a direct current potentiometer 31 connected between the two electrodes, a potential difference between the electrodes is measured so as to determine the membrane potential, namely, the response potential. The sample water 34 is stirred by an agitator 35. In a device as described above, a potential difference in accordance with the lithium ion concentration in the sample water can be obtained on the direct current potentiometer. Accordingly, a calibration curve can be determined using a sample water having a known concentration of lithium ions.

Figure 8:
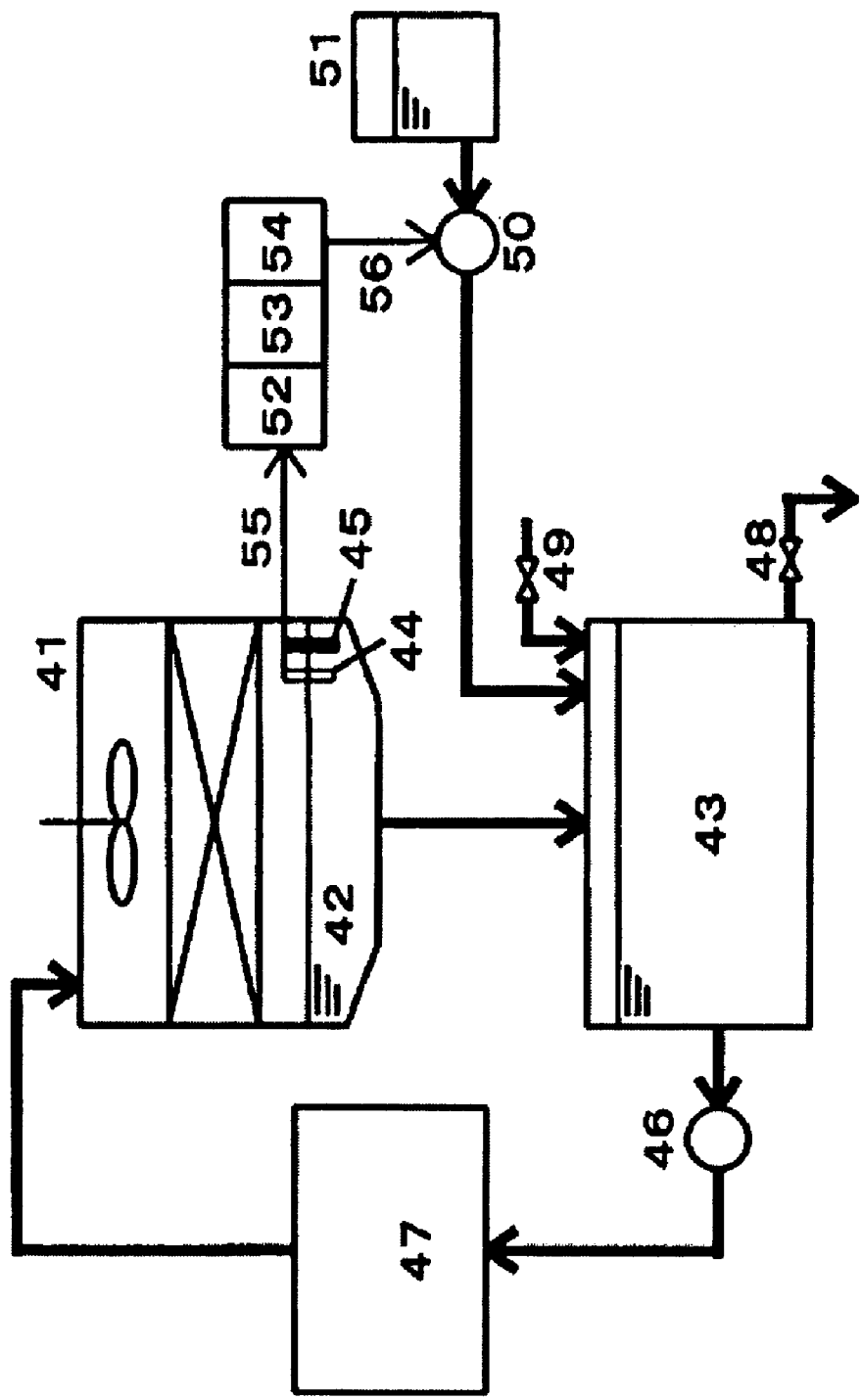
FIG. 8 shows one example of an apparatus for controlling concentration of a water treatment chemical using a lithium ion electrode, and schematically illustrates use of this apparatus in a cooling water system.

FIG. 8 shows an example apparatus for controlling concentration of a water treatment chemical using a lithium ion electrode according to the present invention, and schematically illustrates use of this apparatus in a cooling water system. This apparatus for controlling concentration of a water treatment chemical comprises a lithium ion electrode 44, a reference electrode 45, a receiving section 52 for receiving a signal from the lithium ion electrode 44 via a receiving signal line 55 and determining a response potential, an arithmetic section 53 for calculating a water treatment chemical concentration based on the response potential value, and a control section 54 for determining, based on the calculated water treatment chemical concentration, an amount of water treatment chemical to be added to water to be treated. After determining the dosage level of water treatment chemical, the control section 54 outputs a signal indicating the dosage level via a control signal line 56 to a pump 50 for injecting water treatment chemical. The pump 50 is driven in accordance with the signal to inject an appropriate amount of water treatment chemical into a cooling water tank 43.

In this arrangement, the configuration of the lithium ion electrode is as previously described. The lithium ion electrode and the reference electrode may be formed as separate electrodes, or may alternatively be integrated as one composite electrode. Further, for the purpose of measuring water temperature, a temperature sensor is preferably provided near the lithium ion electrode. More preferably, for installation convenience, a temperature sensor is integrated inside the composite electrode noted above. Although the lithium ion electrode may be placed in a flow cell in which sample water is partially extracted and allowed to flow from the cooling water system, such an arrangement requires additional facilities such as a water sampling line and a flow cell. The lithium ion electrode is therefore preferably placed directly in a cooling water pit, cooling water tank, or cooling water piping of the cooling water system.

As the receiving section 52 for receiving a signal from the lithium ion electrode 44 and the reference electrode 45, a typical direct current potentiometer may be used. However, in order to minimize current flow in the lithium ion electrode 44 so as to stabilize measurement values, it is particularly preferable to use a direct current potentiometer having a high input impedance of $10^{11}\Omega$ or greater. The receiving section 52 functions as the transducer for converting into an electric signal a state (potential) of the lithium ion sensitive membrane including the lithium ion sensitive substance.

The arithmetic section 53 converts a signal indicating the response potential determined by the receiving section 52 into a lithium ion concentration within water to be treated, using a calibration curve stored in advance. Further, the arithmetic section 53 calculates, using the above-described chemical concentration conversion coefficient, the water treatment chemical concentration within water to be treated.

The control section 54 employs the lithium ion concentration and/or water treatment chemical concentration calculated in the arithmetic section 53 to control the pump 50 for adding the lithium ion and/or water treatment chemical.

While the receiving section 52, arithmetic section 53, and control section 54 have independent functions, they may be configured as one unit. The arithmetic section 53 and control section 54 are preferably configured using a programmable controller, computer, or the like.

EXAMPLES

The present invention will next be described more specifically referring to examples. It should be noted that the present invention is not limited to these examples.

The fabrication procedure of a lithium ion electrode and its method of use employed for Example 1 are first explained below.

[Fabrication and Method of Use of Lithium Ion Electrode]

In Example 1, a lithium ion electrode as shown in FIG. 2 was used. This lithium ion electrode comprised an electrode line 1, a outer plastic tube 2 (tube composed of poly(vinyl chloride)), and a sensitive membrane 3. The sensitive membrane 3 comprised a paste material formed by mixing 6,6-dibenzyl-1,4,8,11-tetraoxacyclotetradecane denoted by chemical formula (3), 2-nitrophenyloctylether, and graphite powder. The substance of chemical formula (3) was the lithium ion selective coordination molecules which selectively form coordinate bonds with lithium ions. Percentage content for each substance was 1–5 weight percent for 6,6-dibenzyl-1,4,8,11-tetraoxacyclotetradecane, 40 wt % for 2-nitrophenyloctyl ether, and 55–59 wt % for graphite powder. The lithium ion electrode formed as above was used in combination with a reference electrode in the form of a saturated potassium chloride/silver-silver chloride electrode. The two electrodes were immersed in water to be treated, which is the subject of measurement. Electromotive force generated between the two electrodes was measured using a millivolt meter.

Example 1

In order to verify the effectiveness of the present method employing a lithium sensitive substance to measure concentration of lithium ions, an experiment was conducted in an open recirculating cooling water system.

[Open Recirculating Cooling Water System]

The operating conditions of the openreccirculating cooling water system used for the present experiment were as below.

Raw water: industrial water of Toda City, Saitama Prefecture, Japan.

Amount of water retained: 2 tons.

Recirculation Rate: 1 ton/minute.

Water temperature at the cooling water inlet of the heat exchanger: 25° C.

Water temperature at the cooling water outlet of the heat exchanger: 35° C.

The quantity of water equivalent to the amount of evaporated water and drifted water was supplemented using Toda City industrial water. The cycles of concentration was calculated using the ratio of electric conductivity values of the raw water (make-up water) and the cooling water, and controlled to be maintained within the range of 2–2.5.

[Experiment]

A water treatment chemical containing, as tracers, sodium bromide and lithium carbonate each by its predetermined amount was added to the cooling water system, and the cooling water was recirculated. Measurements of bromide ion concentration and lithium ion concentration were made over time, and compared in the form of detected concentration percentages while assuming that the detected concentrations of the respective substances measured immediately after adding were 100%. The bromide ion concentration was measured by ion chromatography (industrial water testing method 34.2 of Japan Industrial Standards (JIS) K 0101). The lithium ion concentration was measured by atomic absorption method (pursuant to the industrial water testing method 47.2 of JIS K 0101 for measuring sodium ion, while replacing the atomic absorption wavelength 589.0 nm for Na with the atomic absorption wavelength 670.8 nm for Li) and the above-described lithium ion electrode method. The composition of the water treatment chemical is shown in Table 1. In Table 1, Dequest 2010 is ethylene diphosphonate distributed by Monsanto Japan Ltd., Acumer 2000 is a sulfonated acrylate copolymer manufactured by Rohm and Haas Company, and Kathon WT is an isothiazolone antimicrobial manufactured by Rohm and Haas Company.

TABLE 1

| Chemical agent (Product name) | Function | Weight % |
| --- | --- | --- |
| benzotriazole | corrosion inhibitor | 0.5 |
| Dequest 2010 | corrosion inhibitor | 2.5 |
| Acumer 2000 | dispersant | 2.5 |
| Kathon WT | antimicrobial | 2.7 |
| lithium carbonate | tracer | 0.05 |
| sodium bromide | tracer | 2.5 |

As a result, as shown in Table 2, it was observed that the behavior of the lithium ion concentration values measured using the lithium ion electrode closely coincided with the behaviors of the bromide ion concentration values measured by the ion chromatography method and the lithium ion concentration values measured by the atomic absorption method. Based on this result, it was verified that the present method can be equivalently used as the conventional bromine tracer method employing ion chromatography and the lithium ion tracer method employing the atomic absorption method. While the ion chromatography method and the atomic absorption method required time for collecting sample water, delivering the sample water to the ion chromatograph or the atomic spectrometer, and at least 1–2 hours for analysis, the lithium ion electrode method according to the present invention could output measurement values for on-site confirmation without requiring much time. Accordingly, the present method was proved to be sufficiently effective in real-time automatic control of a chemical concentration.

TABLE 2

| | Lithium ions | | |
|---|---|---|---|
| Elapsed time (days) | Lithium ion selective electrode method | Atomic absorption method | Bromide ions Ion chromatography |
| 0 | 100% | 100% | 100% |
| 1 | 96% | 97% | 98% |
| 3 | 95% | 96% | 97% |
| 5 | 94% | 94% | 95% |
| 7 | 94% | 95% | 95% |

Next described are the fabrication procedure of lithium ion electrodes and their method of use employed for Reference Cases 1–4 and Example 2.

[Fabrication and Method of Use of Lithium Ion Electrodes]

In each of Reference Cases 1–4 and Example 2, a lithium ion electrode as shown in FIG. 3 was used. The lithium ion electrode comprised an internal reference electrode 11, an internal solution 13, and a sensitive membrane 14. A silver-silver chloride electrode was used as the internal reference electrode 11. As the internal solution a 13, 0.01 mol/L LiCl aqueous solution was employed. The sensitive membrane 14 was produced by first dissolving lithium ion selective coordination molecules and an anion eliminator in a membrane solvent, and adding thereto a terahydrofuran solution containing dissolved poly(vinyl chloride). The mixture was stirred well and subsequently spread on a glass plate to be air-dried, so as to form a membrane. A membrane piece having a diameter of 6 mm was cut out from the membrane and attached to an outer tube 12. The internal reference electrode 11 and the outer tube 12 were components included in a commercially available liquid membrane type ion electrode kit (manufactured by DKK-TOA Corporation).

The sensitive membrane was a liquid membrane having a composition as shown in Table 3. The anion eliminator was K-TCPB (manufactured by Dojindo Laboratories). The membrane solvent was NPOE (manufactured by Dojindo Laboratories). As the lithium ion selective coordination molecules, compounds of chemical formulas (3), (4), (5), and (6) were separately employed in the respective lithium ion electrodes. The compounds of chemical formulas (3), (4), and (6) were manufactured by Dojindo Laboratories. The compound of chemical formula (5) was synthesized according to a method disclosed in Japanese Patent Laid-Open Publication No. Hei 6-73045 and Anal. Chem., 65, 3404–3410 (1993).

TABLE 3

| Component | Composition ratio (wt %) |
|---|---|
| lithium ion selective coordination molecules | 3.0 |
| membrane solvent | 60.0 |
| poly(vinyl chloride) | 36.3 |
| anion eliminator | 0.7 |

A lithium ion electrode formed as above and a double junction type reference electrode (manufactured by DKK-TOA Corporation; Model No. 4083) were connected to a direct current potentiometer (manufactured by DKK-TOA Corporation; Model No. IM-55G). The lithium ion electrode and the reference electrode were immersed in sample water or water to be treated, and a potential difference between the two electrodes was measured by the direct current potentiometer as the response potential.

The experiments of Reference Cases 1–4 were conducted under the following conditions. Lithium chloride was used as the lithium ion source. The raw water of the open recirculating cooling water system was the above-noted Toda City industrial water. The water temperature was controlled so as to be maintained constant at 25° C. Measurement of the response potential was conducted using a device as shown in FIG. 7. The ratio of electric conductivity values of the raw water (make-up water) and the cooling water (concentrated water) was used to calculate the cycles of concentration.

Reference Case 1 (Measurement Example Using a Lithium Ion Electrode Having a Sensitive Membrane Including the Compound of Chemical Formula (3))

Figure 9:
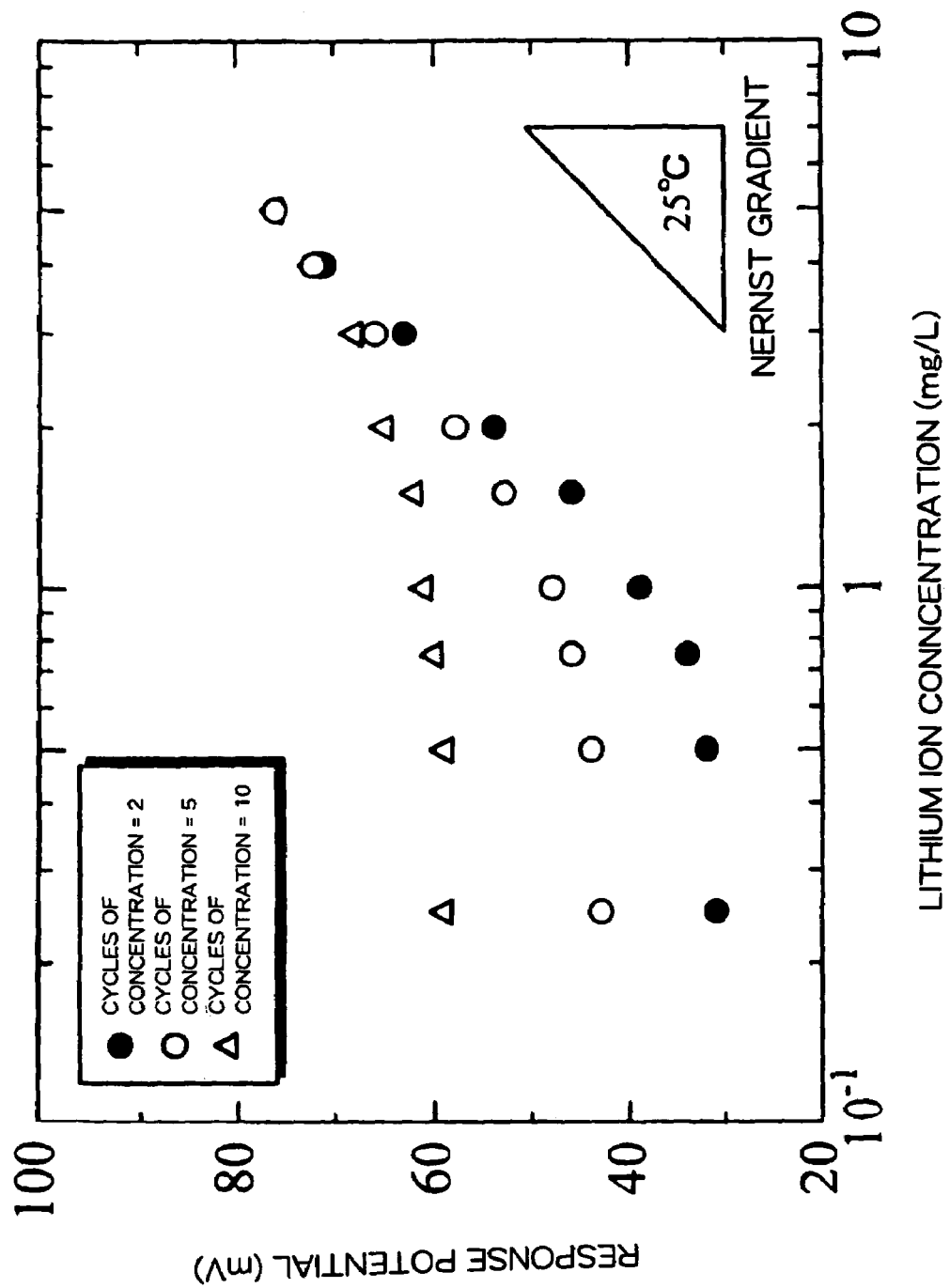
FIG. 9 is a graph showing measurements of response potential obtained using a lithium ion electrode having a sensitive membrane including a compound of chemical formula (3). The graph of FIG. 9 indicates that the relationship between the response potential values indicated by the lithium ion electrode and the lithium ion concentration exhibits a dependency on the water concentration ratio.

Measurements of response potential values were made using a lithium ion electrode having a sensitive membrane including the compound of chemical formula (3), so as to determine whether the relationship between the response potential values indicated by the lithium ion electrode and the lithium ion concentration was dependent on the water cycles of concentration. As the subject of measurement, which corresponds to water to be treated, water samples were prepared by collecting water having varying cycles of concentration of 2, 5, and 10 from the open recirculating cooling water system, and adding thereto lithium chloride such that predetermined lithium ion concentrations were obtained. Response potential values were measured for the respective water samples, and the measured results were as shown in FIG. 9. As can be seen in FIG. 9, the behavior of response potential values strongly depended on the sample water cycles of concentration. In other words, when using a lithium ion electrode having a sensitive membrane including the compound of chemical formula (3), a measured response potential is greatly influenced by the cycles of concentration. It was therefore understood that, with respect to a system in which the cycles of concentration of water to be treated such as cooling water vaies and with respect to a plurality of systems having different water cycles of concentration, measurement of lithium ion concentration in water to be treated based on the above-noted equation 1 or 2 would not be very accurate when a lithium ion electrode including the compound of chemical formula (3) is used.

Reference Case 2 (Measurement Example Using a Lithium Ion Electrode Having a Sensitive Membrane Including the Compound of Chemical Formula (4))

Figure 10:
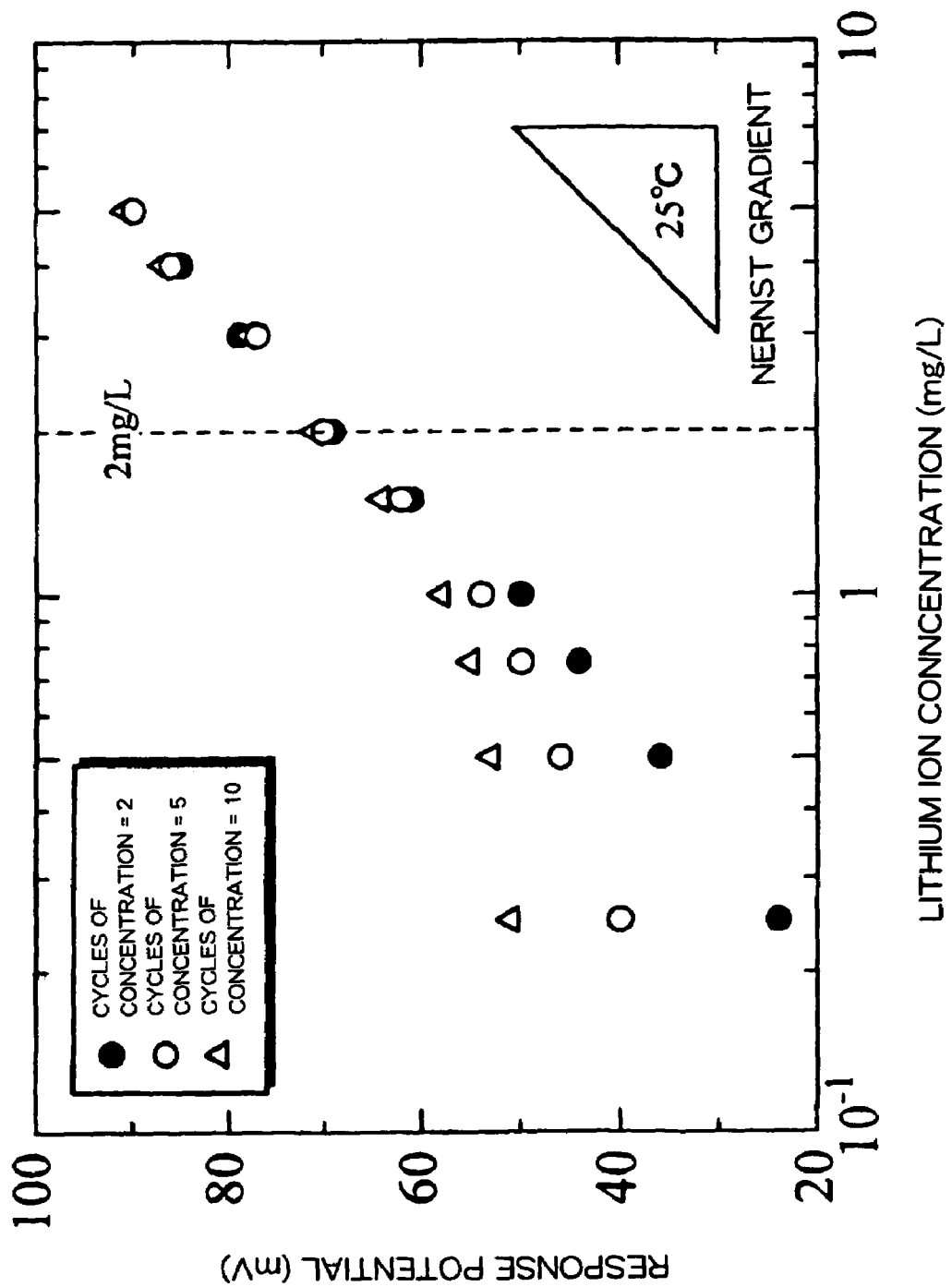
FIG. 10 is a graph showing measurements of response potential obtained using a lithium ion electrode having a sensitive membrane including a compound of chemical formula (4). The graph of FIG. 10 indicates that the relationship between the response potential values indicated by the lithium ion electrode and the lithium ion concentration exhibits a dependency on the water concentration ratio.

A test almost identical to Reference Case 1 was conducted, while the lithium ion electrode including the compound of chemical formula (3) was replaced with a lithium ion electrode having a sensitive membrane including the compound of chemical formula (4). As can be observed from the obtained results shown in FIG. 10, in the region in which the lithium ion concentration is greater than or equal to 1 mg/L, the response potential gradient became close to the Nernst gradient regardless of the cycles of concentration of the water samples, and no influence from the cycles of concentration was observed when the lithium ion concentration was 2 mg/L or higher. In other words, when a lithium ion electrode having a sensitive membrane including the compound of chemical formula (4), which is one of the compounds denoted by chemical formula (1), is employed, and the concentration of lithium ions added as the tracer substance to water to be treated is 2 mg/L or lower, lithium ion concentration in water to be treated such as cooling water can be measured at an accuracy higher compared to when using a lithium ion electrode including the compound of chemical formula (3), without receiving influences from the cycles of concentration. It should be noted that, according to the present case, addition of lithium ions at a concentration exceeding 2 mg/L results in using unnecessary lithium ions, which is uneconomical.

Reference Case 3 (Measurement Example Using Deionized Water)

Figure 11:
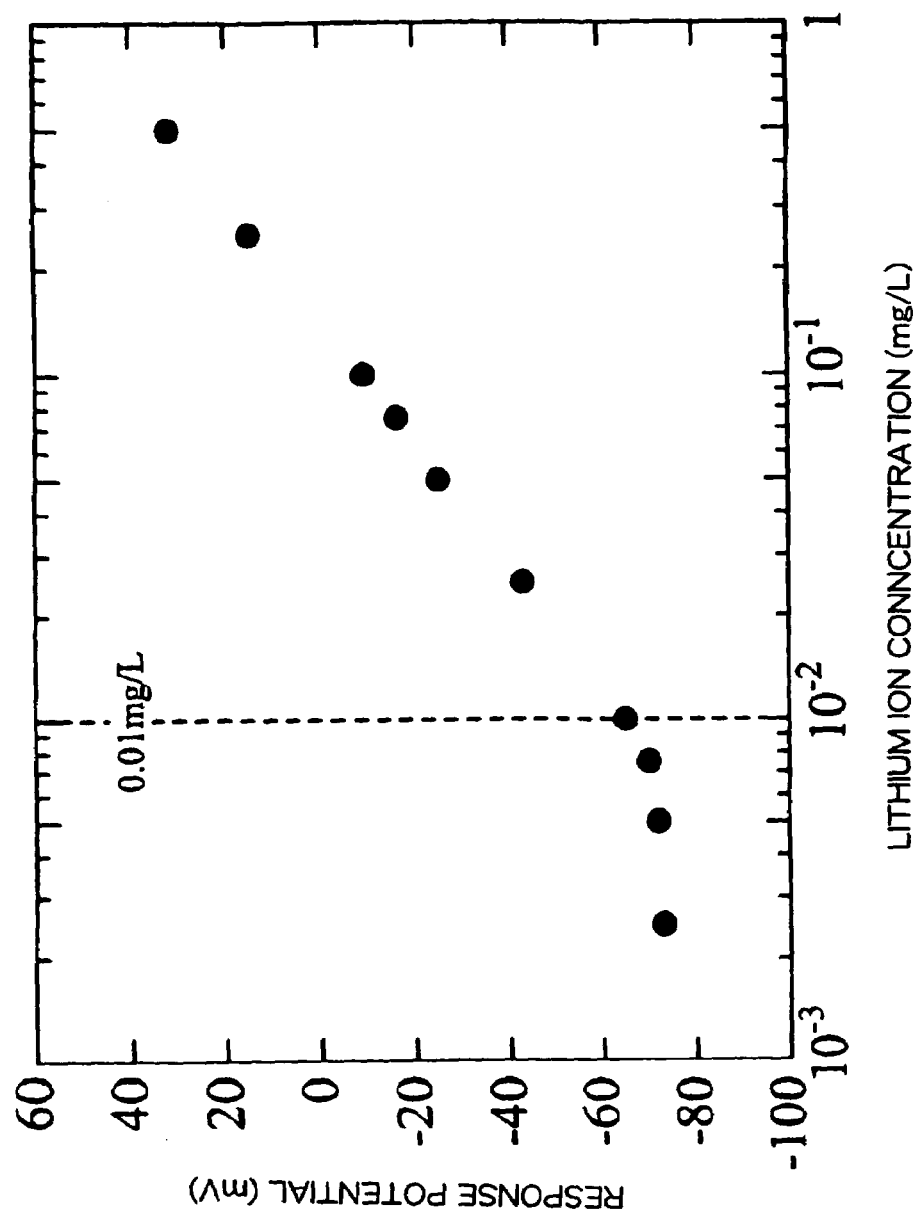
FIG. 11 is a graph showing measurements of response potential obtained using a lithium ion electrode having a sensitive membrane including a compound of chemical formula (4) while employing deionized water as the sample water. The graph of FIG. 11 illustrates a relationship between the response potential values indicated by the lithium ion electrode and the lithium ion concentration.

As noted above, deionized water is employed as the raw water in some cooling water systems. Accordingly, water samples were prepared by adding, to deionized water, lithium chloride such that predetermined lithium ion concentrations were obtained. Response potential values were then measured using a lithium ion electrode identical to the ion electrode employed in the above Reference Case 2. As can be observed from the measured results shown in FIG. 11, the Nernst gradient is not exhibited in the lithium ion concentration region below 0.01 mg/L. It was therefore understood that, with respect to the purpose of controlling water treatment chemical concentration, lithium ions cannot sufficiently function as the tracer substance when the lithium ion concentration within the cooling water system is less than or equal to 0.01 mg/L.

Reference Case 4 (Measurement Example Using Water Having a Concentration Ratio of 10)

Figure 12:
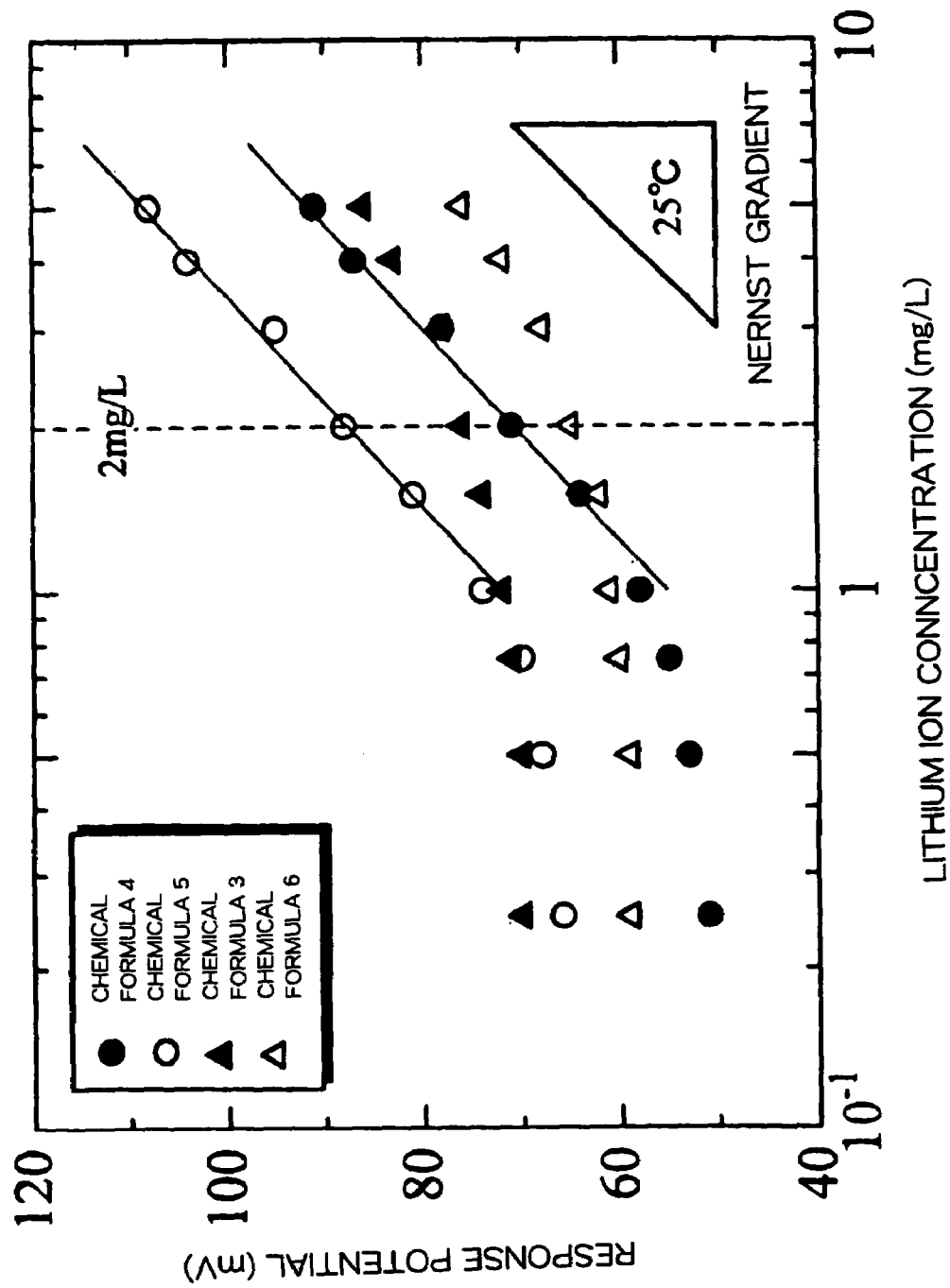
FIG. 12 is a graph showing measurements of response potential obtained using lithium ion electrodes each having a sensitive membrane including a compound of one of chemical formulas (3)–(6) while employing water having a concentration ratio of 10 as the sample water. The graph of FIG. 12 illustrates relationships between the response potential values indicated by the respective lithium ion electrodes and the lithium ion concentration.

Measurements of response potential values were made using lithium ion electrodes each including the compound of chemical formula (3), (4), (5), or (6). Water samples were prepared by collecting water having a cycles of concentration of 10 from the open recirculating cooling water system, and adding thereto lithium chloride such that predetermined lithium ion concentrations were obtained. Response potential values were measured for the respective water samples, and the measured results were as shown in FIG. 12. As can be observed, when a lithium ion electrode employing the compound of chemical formula (4) or (5) is used, the Nernst gradient is exhibited, even in the lithium ion concentration region below 2 mg/L. However, when a lithium ion electrode employing the compound of chemical formula (3) or (6) is used, the Nernst gradient is not exhibited, such that the lithium ion concentration cannot be accurately calculated from the response potential according to the present method. The compound of chemical formula (5) is one of the compounds denoted by chemical formula (2). Accordingly, it can be understood that, when a lithium ion electrode having a sensitive membrane including a compound of chemical formula (2) is employed (similarly as when one of the compounds of chemical formula (1) is included), and the concentration of lithium ions added as the tracer substance to water to be treated is 2 mg/L or lower, lithium ion concentration in water to be treated such as cooling water can be measured at a high accuracy An apparatus as shown in FIG. 8 was used for the experiment of Example 2. The apparatus of FIG. 8 is described as below. Water is cooled in a cooling tower 41 by the latent heat of vaporization generated by evaporated water, and the cooled water is delivered to and temporarily stored in a cooling water tank 43 via a cooling water pit 42. The stored cooling water is delivered by a cooling water circulation pump 46 to a heat exchanger 47 to perform heat exchange. The water after performing heat exchange is delivered to the cooling tower 41. The cooling water is thus circulated. According to necessity, make-up water is supplied to the cooling water tank 43 via a make-up water supply valve 49. Further, when necessary, a portion of the cooling water within the cooling water tank 43 is discharged as blowdown via a cooling water blowdown valve 48. A lithium ion electrode 44 and a reference electrode 45 are immersed in the cooling water within the cooling water pit 42. A signal indicating a potential difference between the two electrodes is transmitted to a receiving section 52 via a receiving signal line 55. The receiving section 52 measures the direct current potential difference. Based on the measured value, an arithmetic section 53 calculates the concentration of a water treatment chemical. In accordance with the calculated water treatment chemical concentration, a control section 54 determines an amount of water treatment chemical to be added to the cooling water. A control signal based on the determined dosage level of water treatment chemical is transmitted via a control signal line 56 to a pump 50 for injecting the water treatment chemical. The pump 50 is controlled by the control signal to inject the water treatment chemical from a water treatment chemical tank 51 to the cooling water tank 43. In this apparatus, it is understood that the water treatment chemical concentration control device according to the present invention is mainly constituted by the lithium ion electrode 44, reference electrode 45, receiving signal line 55, receiving section 52, arithmetic section 53, control section 54, and control signal line 56.

In Example 2, lithium ion selective electrodes each having a sensitive membrane including the compound of chemical formula (4) or (3) were used as the lithium ion electrode 44. As the reference electrode 45, a reference electrode of internal liquid non-refill type (manufactured by DKK-TOA Corporation; Model No. 4401L) was employed. The lithium ion and reference electrodes were connected to a direct current potentiometer (manufactured by DKK-TOA Corporation; Model No. IM-55G). The response potential was output from the direct current potentiometer as an analog voltage value. This signal was input into a control device including an analog-to-digital converter, microcomputer, and solid-state relay, to thereby control the pump 50 for injecting water treatment chemical. In this arrangement, the direct current potentiometer and the analog-to-digital converter correspond to the receiving section 52, a portion of the microcomputer 53 corresponds to the arithmetic section 53, and a portion of the microcomputer 53 and the solid-state relay corresponds to the control section 54. Further, because the temperature of recirculating water (cooling water) varies in this type of apparatus, in the experiment of Example 2, a water temperature sensor was provided near the lithium ion electrode, and an output signal from the sensor was input into the control device. Furthermore, to record the experiment, each of the response potential and the water temperature information was output as an analog signal to an external device other than the control device via a digital-to-analog converter, and recorded by a recorder.

In the microcomputer, $S(T)$ and $E_0$ values determined in advance based on an input water temperature information were used to calculate a lithium ion concentration based on an input response potential. Further, based on the calculated lithium ion concentration and a chemical concentration conversion coefficient, a concentration value of the water treatment chemical within water to be treated was determined. By comparing the determined value with a preset target value of water treatment chemical concentration, a signal for controlling ON/OFF of the pump for injecting water treatment chemical was produced. Within the control device, the solid-state relay operated in accordance with the ON/OFF information to turn on and off the power of the pump for injecting water treatment chemical.

Example 2

In order to verify the effectiveness of the present method and apparatus, experiments were conducted in an open recirculating cooling water system. A lithium ion selective electrode having a sensitive membrane including the compound of chemical formula (4) was first employed.

[Open Recirculating Cooling Water System]

The operating conditions of the open recirculating cooling water system used for the present experiment were as below.

Raw water: industrial water of Toda City, Saitama Prefecture, Japan.
Amount of water retained: 2 tons.
Recirculation Rate: 1 ton/minute.
Water temperature at the cooling water inlet of the heat exchanger: 25° C.
Water temperature at the cooling water outlet of the heat exchanger: 35° C.

The quantity of water equivalent to the amount of evaporated water and drifted water was supplemented using Toda City industrial water.

[Experiment]

The composition of the water treatment chemical used for the present experiment was as shown in Table 4. Lithium chloride was used as the lithium ion source which served as the tracer substance.

TABLE 4

| Component | Function | Composition ratio (wt %) |
|---|---|---|
| soft water | solvent | 58 |
| 85 wt % phosphoric acid | corrosion inhibitor | 10 |
| 50 wt % zinc chloride aqueous solution | corrosion inhibitor | 20 |
| lithium chloride | tracer substance | 12 |

12 wt % lithium chloride is equivalent to approximately 2 wt % lithium ions by conversion. Accordingly, the concentration conversion coefficient of the water treatment chemical of Table 4 with respect to the lithium ion concentration was 50. The target control concentration of this water treatment chemical was 50 mg/L. Accordingly, it was appropriate to maintain the lithium ion concentration in the cooling water at 11.0 mg/L.

Figure 13:
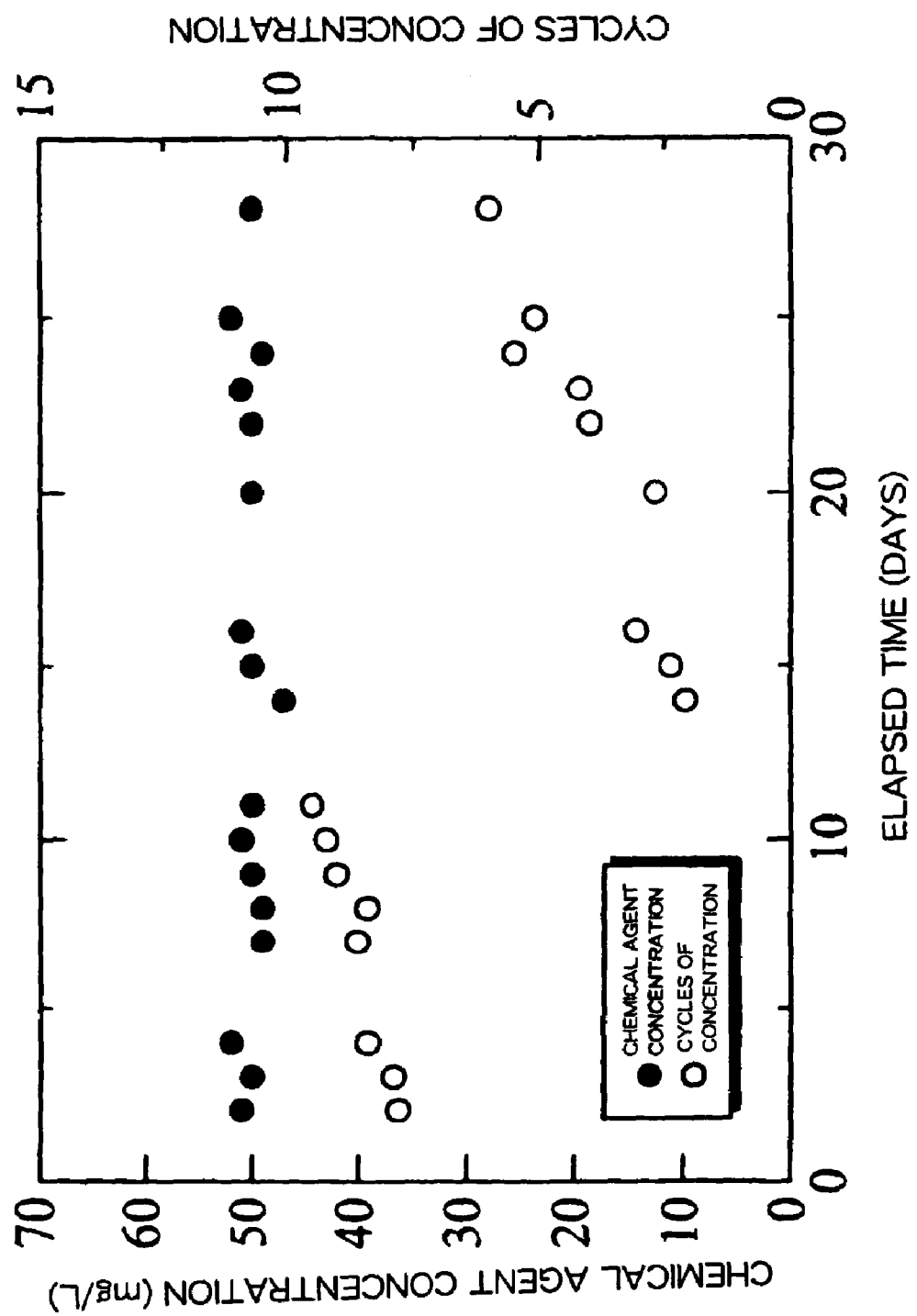
FIG. 13 is a graph showing experimental results obtained in an open circulated cooling water system using a lithium ion electrode having a sensitive membrane including a compound of chemical formula (4).

The above water treatment chemical was supplied in the water treatment chemical tank 51, and the water treatment chemical concentration was controlled using the above-described control device. The cooling water was sampled over time to measure the water treatment chemical concentration (chemical agent concentration) and the cycles of concentration. The cycles of concentration ratio was calculated using the ratio of electric conductivity values of the raw water (make-up water) and the cooling water. Because phosphorus was included in the water treatment chemical, the water treatment chemical concentration was measured and calculated pursuant to the industrial water testing method 43.3.1 of JIS K 0101 1991 for measuring total phosphorus. The obtained results shown in FIG. 13 indicate that, even when the characteristics, particularly the cycles of concentration, of water to be treated is fluctuated, the water treatment chemical concentration can be maintained at a constant level without receiving influences from such fluctuations by performing control using a lithium ion electrode having a sensitive membrane including the compound of chemical formula (4).

Figure 14:
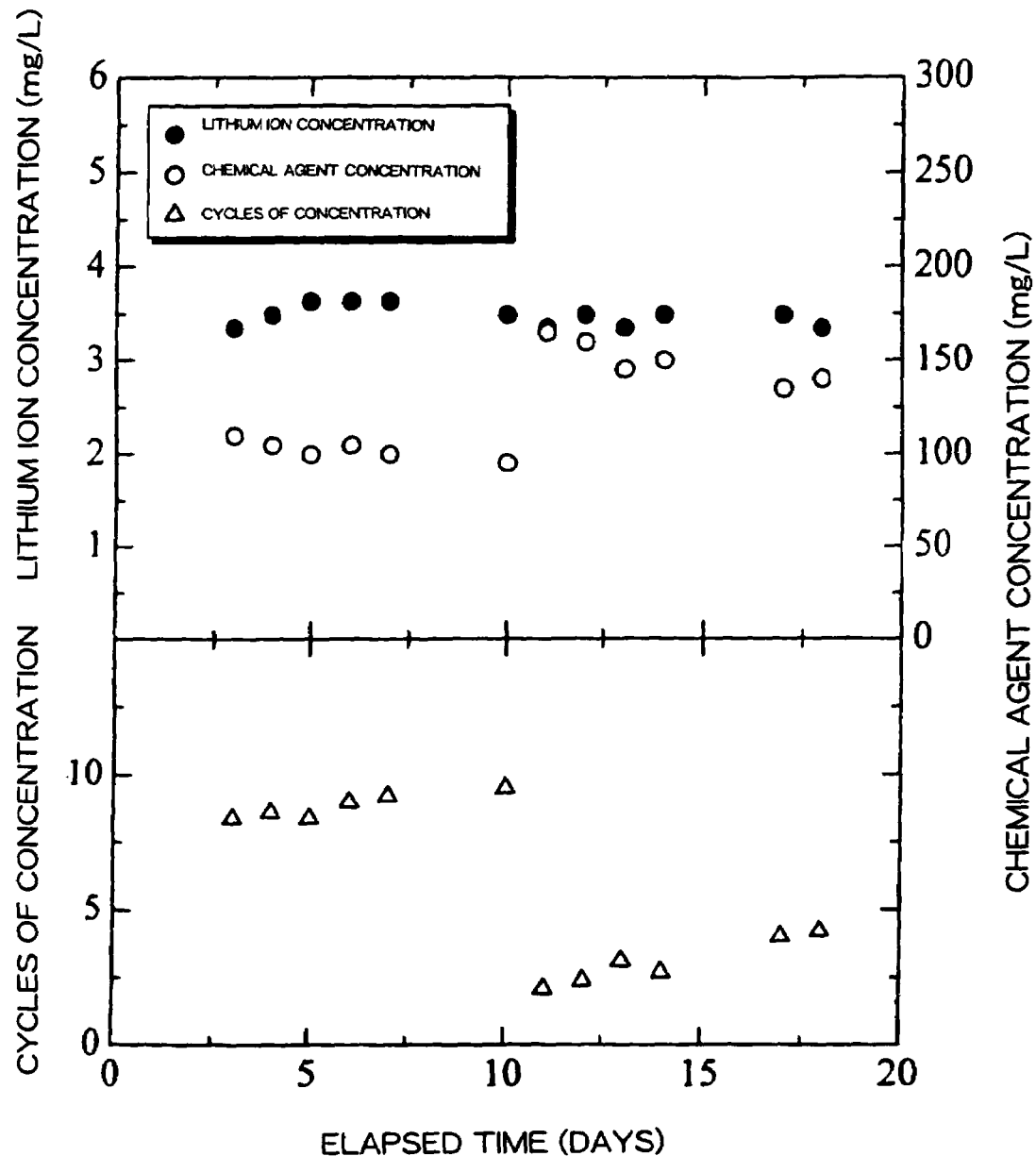
FIG. 14 is a graph showing experimental results obtained in an open circulated cooling water system using a lithium ion electrode having a sensitive membrane including a compound of chemical formula (3).

A further experiment was conducted in the open recirculating cooling water system under the same conditions as above, except that a lithium ion electrode having a sensitive membrane including the compound of chemical formula (3), in place of the compound of chemical formula (4), was employed, and that the target control concentration of the water treatment chemical was set at 175 mg/L. In this case, it was appropriate to maintain the lithium ion concentration in the cooling water at 3.5 mg/L. The obtained results were as shown in FIG. 14. Although the lithium ion concentration values measured by the lithium ion electrode were constantly maintained around 3.5 mg/L, the actual water treatment chemical concentration (chemical agent concentration) dropped far below 175 mg/L. It can be observed that the water treatment chemical concentration was fluctuated by the influences of the cycles of concentration. It is therefore understood that, in a cooling water system having a varying cycles of concentration, a method and apparatus using a lithium ion electrode having a sensitive membrane including the compound of chemical formula (4) can maintain the water treatment chemical concentration at a constant level more easily compared to a method and apparatus using a lithium ion electrode having a sensitive membrane including the compound of chemical formula (3).

By employing a method using a tracer substance for controlling concentration of a water treatment chemical in a recirculated water system such as cooling water system according to an embodiment of the present invention, concentration of a water treatment chemical added to a water system can be measured easily, quickly, and accurately even when the water system receives influences of light or the like which obstruct accurate concentration measurement by conventional tracer methods. Further, according to an embodiment of the present invention, on-site measurements can be made substantially continuously using a simple measurement apparatus, allowing to achieve appropriate control of the water treatment chemical concentration. It should be noted that, while the above explanation was made mainly referring to an open recirculating cooling water system (cooling water tower) as a major example of recirculated water system, a method according to the present invention can also be employed in systems such as a closed recirculatin coolinng water system, a boiler, and an evaporative condenser.

Furthermore, by using a lithium ion electrode incorporating a sensitive membrane including a compound denoted by chemical formula (1) or (2) as the lithium ion sensitive substance, concentration of a water treatment chemical added to a water system can be measured accurately even when the water system exhibits large changes in the characteristics, particularly the cycles of concentration, of water to be treated.

What is claimed is:

1. A method for controlling concentration of a water treatment chemical, comprising
    adding a water-soluble lithium salt as a tracer substance along with the water treatment chemical to water to be treated;
    electrochemically or optically measuring concentration of lithium ions using a lithium ion sensitive substance; and
    using the measured lithium ion concentration to control the concentration of the water treatment chemical added to the water to be treated.

2. A method as defined in claim 1, wherein the lithium ion concentration is measured by detecting a membrane potential indicated by a lithium ion electrode incorporating a sensitive membrane including the lithium ion sensitive substance.

3. A method as defined in claim 2, wherein the lithium ion sensitive substance is a compound denoted by chemical formula (1)

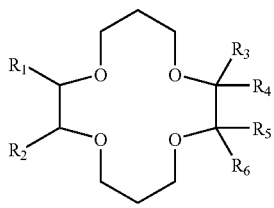

(1)

wherein $R_1$ and $R_2$ are independent from one another, each consisting one of hydrogen atom, alkyl group, benzyl group, benzyloxymethyl group, phenyl group, or cyclohexyl group, and each of $R_3$–$R_6$ is an independent hydrocarbon group.

4. A method as defined in claim 2, wherein the lithium ion sensitive substance is a compound denoted by chemical formula (2)

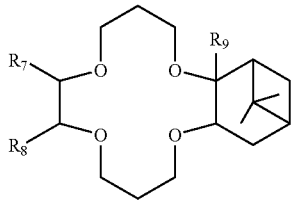

(2)

wherein each of $R_7$–$R_9$ is an independent hydrogen atom or hydrocarbon group, while at least one of $R_7$–$R_9$ is a hydrocarbon group.

5. A method as defined in claim 1, wherein the lithium ion concentration is measured by detecting a change in a value of current flowing in a field effect transistor incorporating the lithium ion sensitive substance.

6. A method as defined in claim 1, wherein the lithium ion concentration is measured by detecting an optical characteristic indicated by a membrane incorporating the lithium ion sensitive substance and a fluorescent or light-absorbing substance.

7. A method as defined in claim 1, wherein the water-soluble lithium salt is added so that the lithium ion concentration in the water to be treated is within the range of 0.01–20 mg/liter.

8. An apparatus for controlling concentration of a water treatment chemical, comprising
a lithium ion sensitive substance placed in contact with water to be treated;
a transducer for converting a state of the sensitive substance into an electric or optical signal;
an arithmetic section for receiving the signal and calculating a concentration of the water treatment chemical; and
a control section for determining, based on the calculated water treatment chemical concentration, an amount of the water treatment chemical to be added to the water to be treated.

9. An apparatus as defined in claim 8, wherein
a sensitive membrane is formed including the lithium ion sensitive substance; and
the sensitive membrane and the transducer constitute a lithium ion electrode.

10. An apparatus as defined in claim 9, wherein the lithium ion electrode includes a light-shielding cover which covers at least the sensitive membrane.

11. An apparatus as defined in claim 9, wherein lithium ion concentration within the water to be treated is measured by detecting a membrane potential indicated by the sensitive membrane.

12. An apparatus as defined in claim 8, wherein the lithium ion sensitive substance is a compound denoted by chemical formula (1)

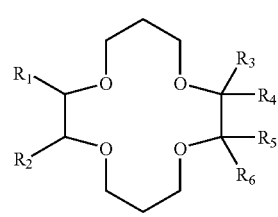

(1)

wherein $R_1$ and $R_2$ are independent from one another, each consisting of one of hydrogen atom, alkyl group, benzyl group, benzyloxymethyl group, phenyl group, or cyclohexyl group, and each of $R_3$–$R_6$ is an independent hydrocarbon group.

13. An apparatus as defined in claim 8, wherein the lithium ion sensitive substance is a compound denoted by chemical formula (2)

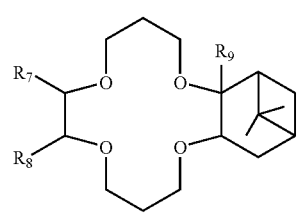

(2)

wherein each of $R_7$–$R_9$ is an independent hydrogen atom or hydrocarbon group, while at least one of $R_7$–$R_9$ is a hydrocarbon group.

14. An apparatus as defined in claim 8, wherein lithium ion concentration is measured by detecting a change in a value of current flowing in a field effect transistor incorporating the lithium ion sensitive substance.

15. An apparatus as defined in claim 8, wherein lithium ion concentration is measured by detecting an optical characteristic indicated by a membrane incorporating the lithium ion sensitive substance and a fluorescent or light-absorbing substance.

* * * * *

UNITED STATES PATENT AND TRADEMARK OFFICE
CERTIFICATE OF CORRECTION

| | | |
|---|---|---|
| PATENT NO. | : 7,105,095 B2 | Page 1 of 1 |
| APPLICATION NO. | : 10/826675 | |
| DATED | : September 12, 2006 | |
| INVENTOR(S) | : Daisaku Yano et al. | |

It is certified that error appears in the above-identified patent and that said Letters Patent is hereby corrected as shown below:

On the Title Page

Under section (75) Inventors, replace "Kiyotaka Yamamura" with

--Kiyotaka Yamaura--.

Signed and Sealed this

Twentieth Day of March, 2007

JON W. DUDAS
*Director of the United States Patent and Trademark Office*